United States Patent
Saltzman et al.

(10) Patent No.: US 10,485,561 B2
(45) Date of Patent: Nov. 26, 2019

(54) ANKLE ARTHROPLASTY SYSTEM AND METHODS

(71) Applicant: Charles Saltzman, Salt Lake City, UT (US)

(72) Inventors: Charles Saltzman, Salt Lake City, UT (US); Albert Burstein, Sparks, NV (US); Jonathan T. Deland, New York, NY (US)

(73) Assignee: LIMACORPORATE S.P.A., Udine (IT)

( * ) Notice: Subject to any disclaimer, the term of this patent is extended or adjusted under 35 U.S.C. 154(b) by 0 days.

(21) Appl. No.: 15/686,079

(22) Filed: Aug. 24, 2017

(65) Prior Publication Data
US 2019/0059917 A1     Feb. 28, 2019

(51) Int. Cl.
| | |
|---|---|
| A61F 2/42 | (2006.01) |
| A61B 17/16 | (2006.01) |
| A61B 17/17 | (2006.01) |
| A61B 17/15 | (2006.01) |
| A61F 2/30 | (2006.01) |

(52) U.S. Cl.
CPC .......... *A61B 17/1682* (2013.01); *A61B 17/15* (2013.01); *A61B 17/1775* (2016.11); *A61F 2/4202* (2013.01); *A61F 2002/30301* (2013.01); *A61F 2002/30884* (2013.01); *A61F 2002/4205* (2013.01); *A61F 2002/4207* (2013.01)

(58) Field of Classification Search
CPC .......... A61F 2/4202; A61F 2002/4205; A61F 2002/4207; A61F 2002/30878; A61F 2002/30301
See application file for complete search history.

(56) References Cited

U.S. PATENT DOCUMENTS

| | | | |
|---|---|---|---|
| 4,156,944 A | * | 6/1979 | Schreiber .............. A61F 2/4202 623/21.18 |
| 5,098,436 A | | 3/1992 | Ferrante |

(Continued)

FOREIGN PATENT DOCUMENTS

| | | |
|---|---|---|
| FR | 2730157 A1 | 8/1996 |
| JP | 2011-115440 A | 6/2011 |

OTHER PUBLICATIONS

International Search Report arid Written Opinion dated Apr. 17, 2019 for corresponding International Application No. PCT/US2017/047944.

*Primary Examiner* — Brian A Dukert
(74) *Attorney, Agent, or Firm* — David Meibos; Maywood IP Law

(57) ABSTRACT

An ankle arthroplasty system may have a talar prosthesis and a tibial prosthesis, each of which has an articular surface and a bone engagement surface. Each bone engagement surface may have an anterior-posterior curvature and a medial-lateral curvature with a convex shape. A burr with a rotatable cutting element may be used to form a prepared surface on the talus or the tibia to receive the corresponding prosthesis. A cutting guide may be used to guide motion of the burr; the cutting guide may include a base and an arm movably coupled to the base. One of the base and the arm may have a guide surface, and the other may have a follower that slides along the guide surface to constrain motion of the burr such that the prepared surface has at least one concave curvature and one convex curvature.

25 Claims, 16 Drawing Sheets

(56) References Cited

U.S. PATENT DOCUMENTS

| | | | |
|---|---|---|---|
| 5,879,354 | A | 3/1999 | Haines |
| 7,625,409 | B2 | 12/2009 | Saltzman et al. |
| 7,963,996 | B2 | 6/2011 | Saltzman et al. |
| 8,491,596 | B2 | 7/2013 | Long et al. |
| 9,119,642 | B2 | 9/2015 | Burstein et al. |
| 9,480,486 | B2 | 11/2016 | Burstein et al. |
| 9,750,516 | B2 | 9/2017 | Tochigi et al. |
| 2006/0229730 | A1* | 10/2006 | Railey .............. A61B 17/15 623/21.18 |
| 2006/0247788 | A1 | 11/2006 | Ross |
| 2012/0053591 | A1 | 3/2012 | Haines |
| 2014/0128985 | A1* | 5/2014 | Sanders ............ A61F 2/4225 623/21.18 |
| 2014/0350688 | A1* | 11/2014 | Michel ............. A61F 2/4202 623/21.18 |
| 2016/0008139 | A1* | 1/2016 | Siegler ............ A61F 2/4202 623/21.18 |
| 2017/0143500 | A1 | 5/2017 | Impero et al. |

\* cited by examiner

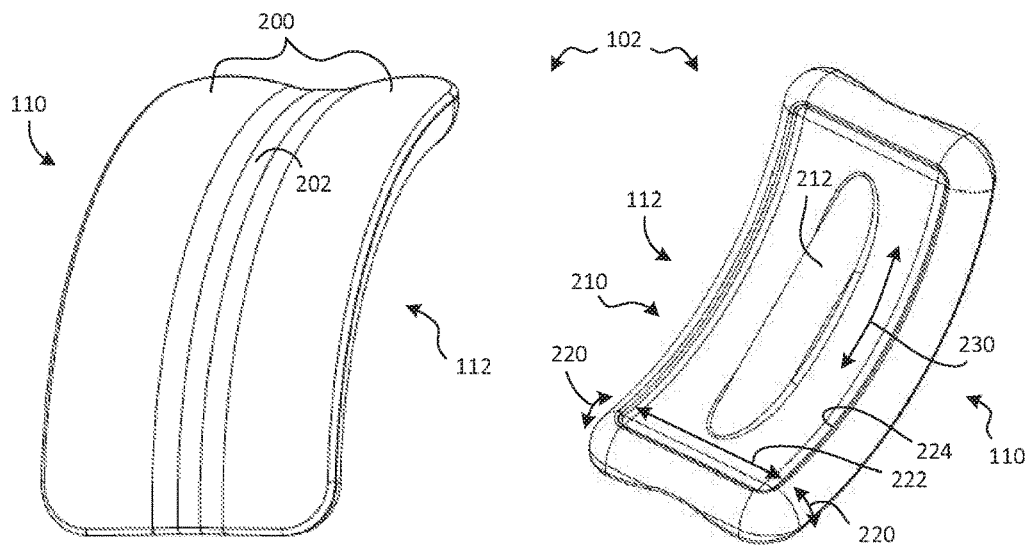
Fig. 2A
Fig. 2B
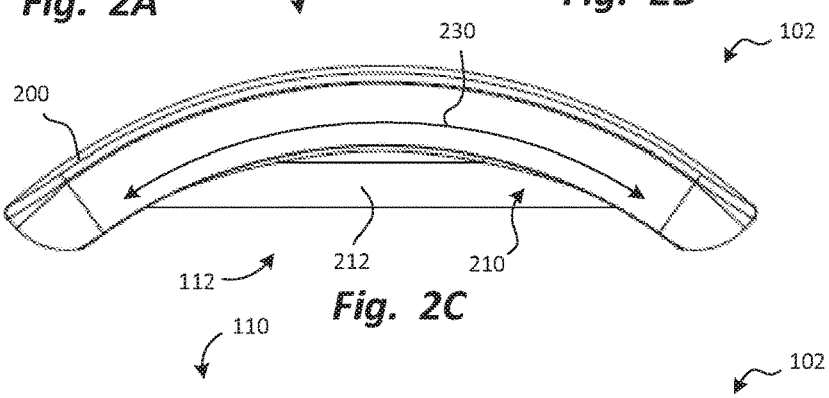
Fig. 2C
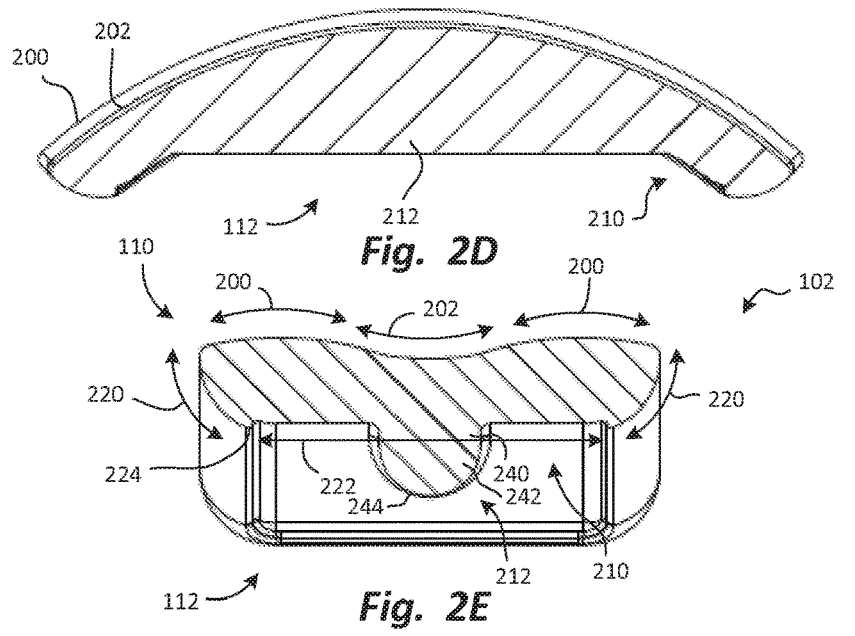
Fig. 2D
Fig. 2E

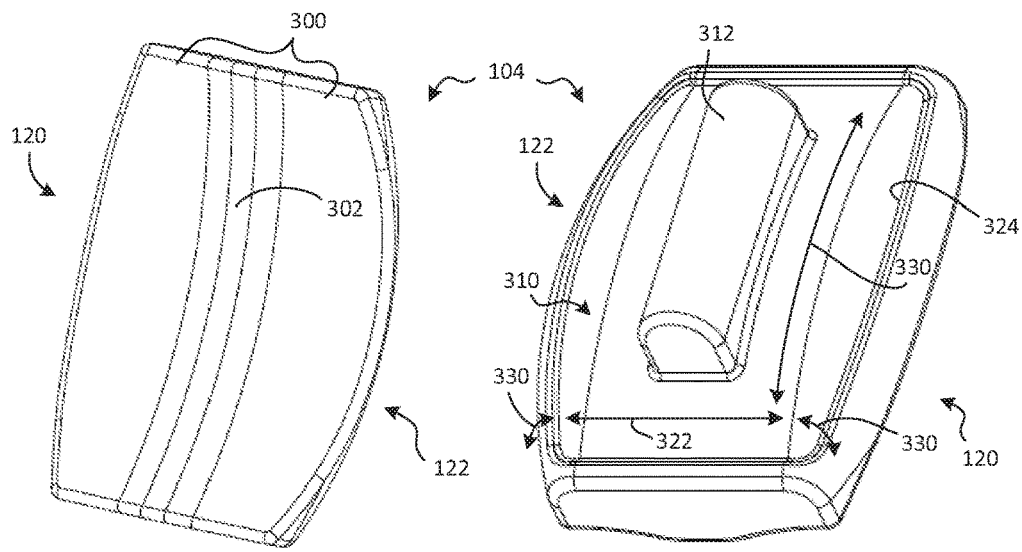
*Fig. 3A*  *Fig. 3B*
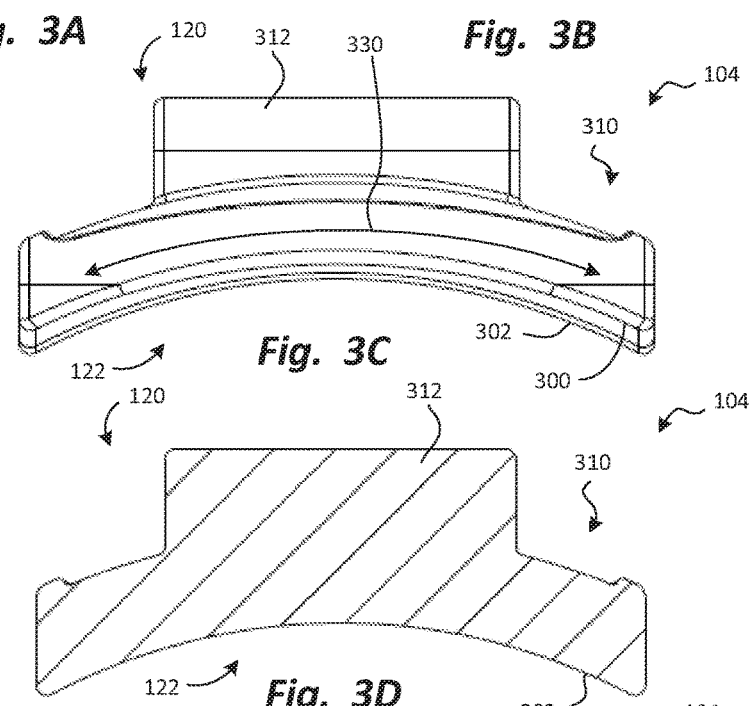
*Fig. 3C*
*Fig. 3D*
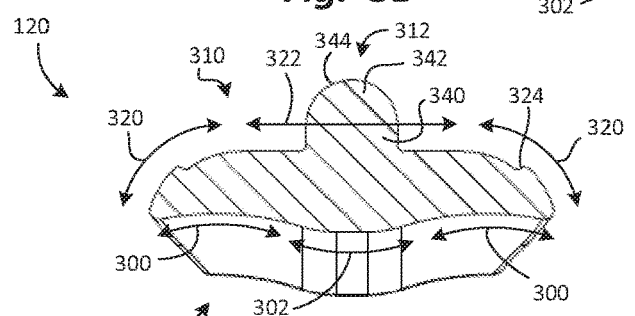
*Fig. 3E*

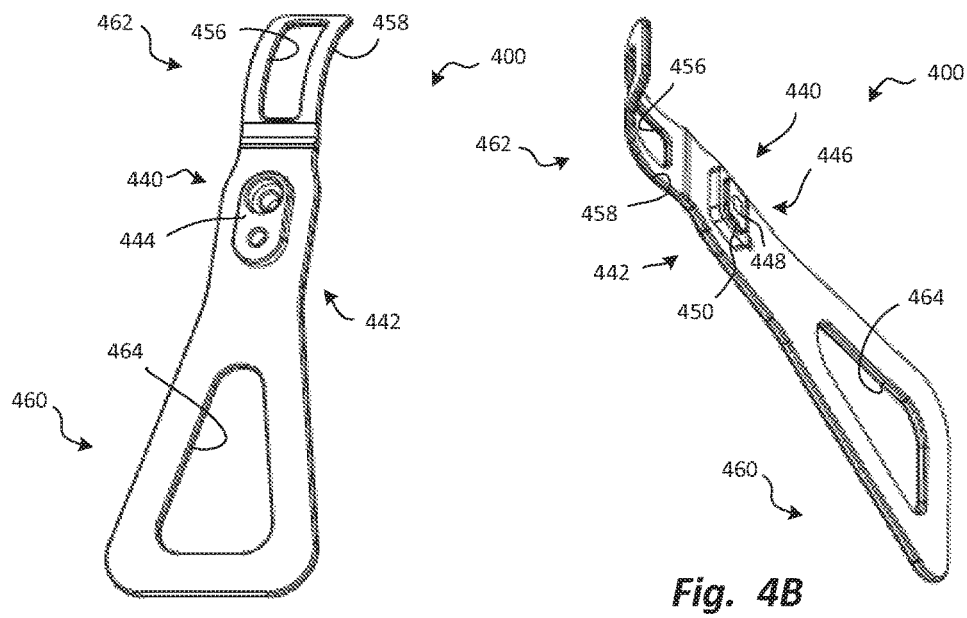
Fig. 4A
Fig. 4B
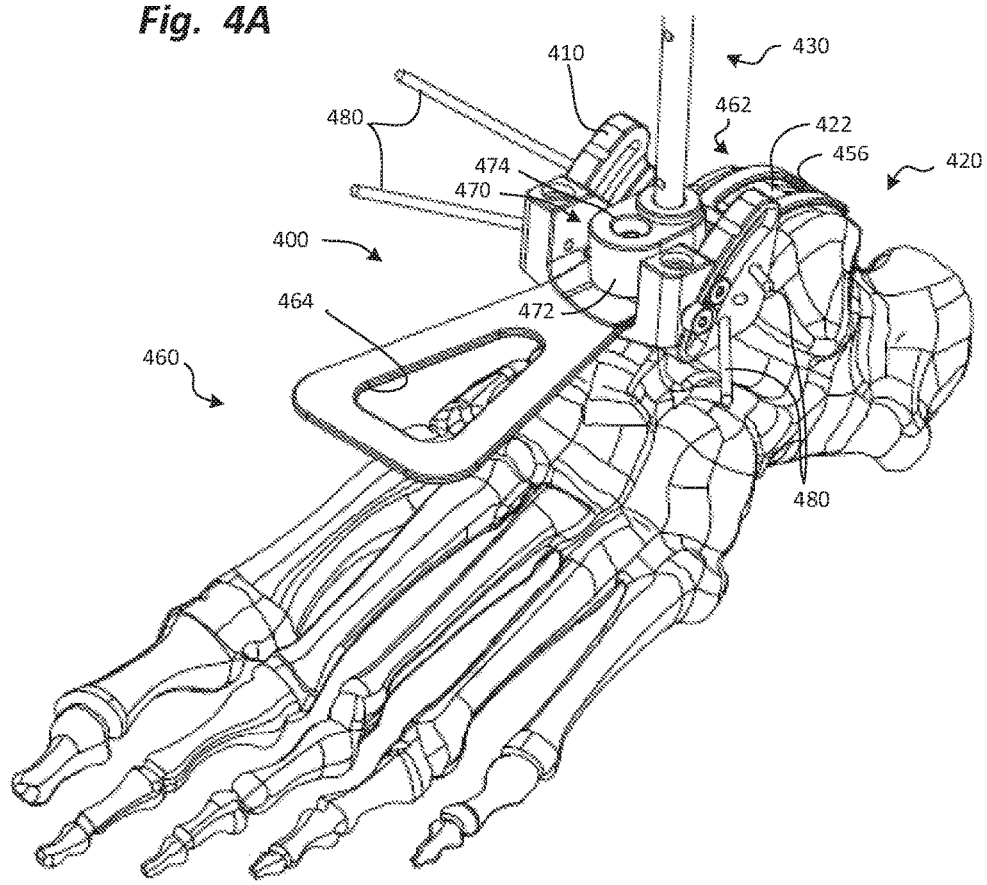
Fig. 4C

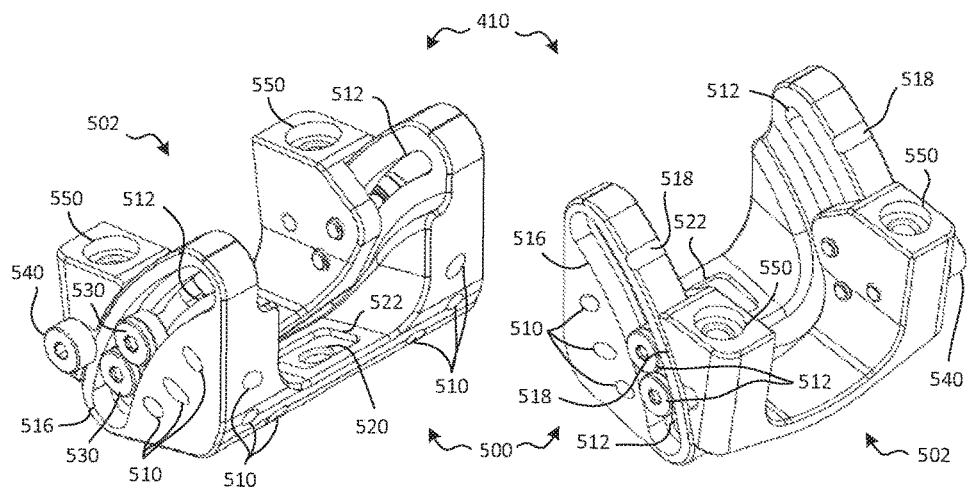
*Fig. 5A*      *Fig. 5B*
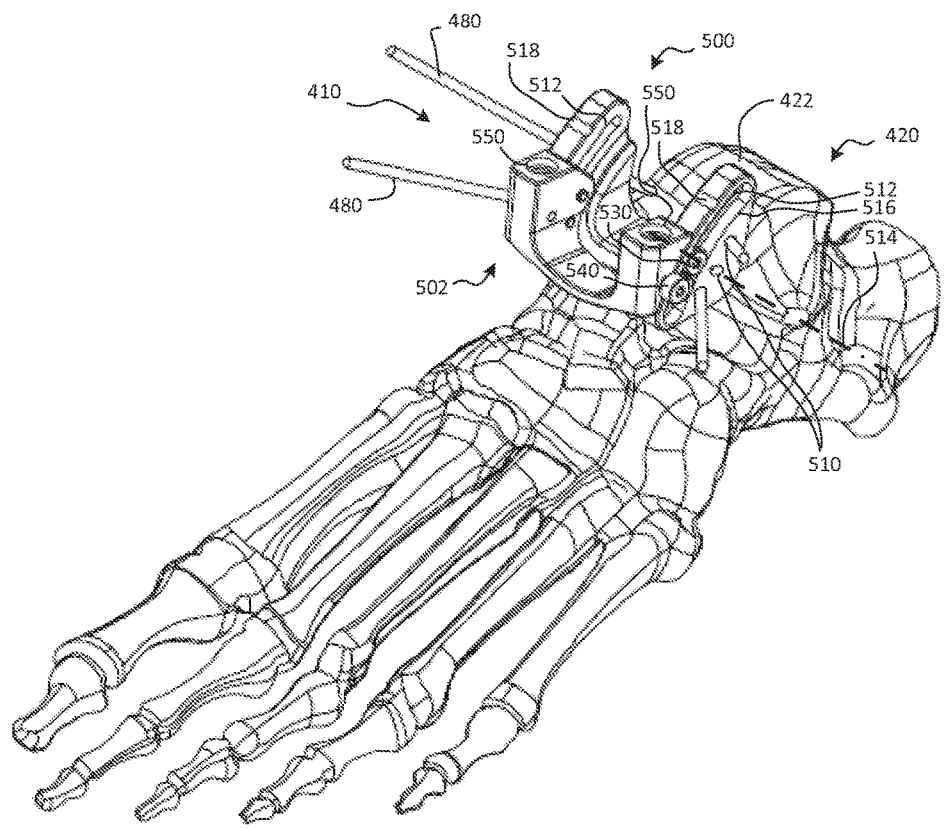
*Fig. 5C*

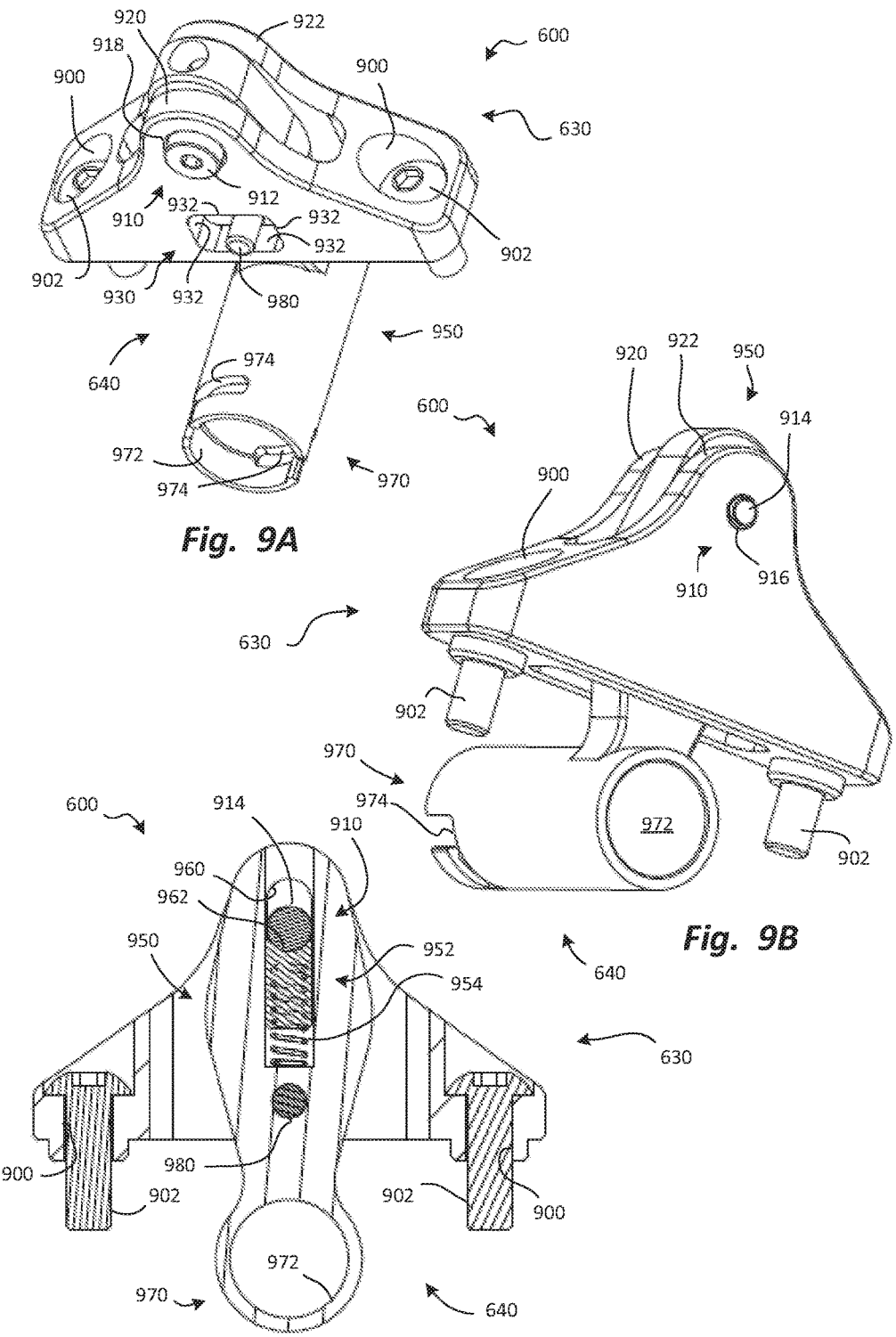

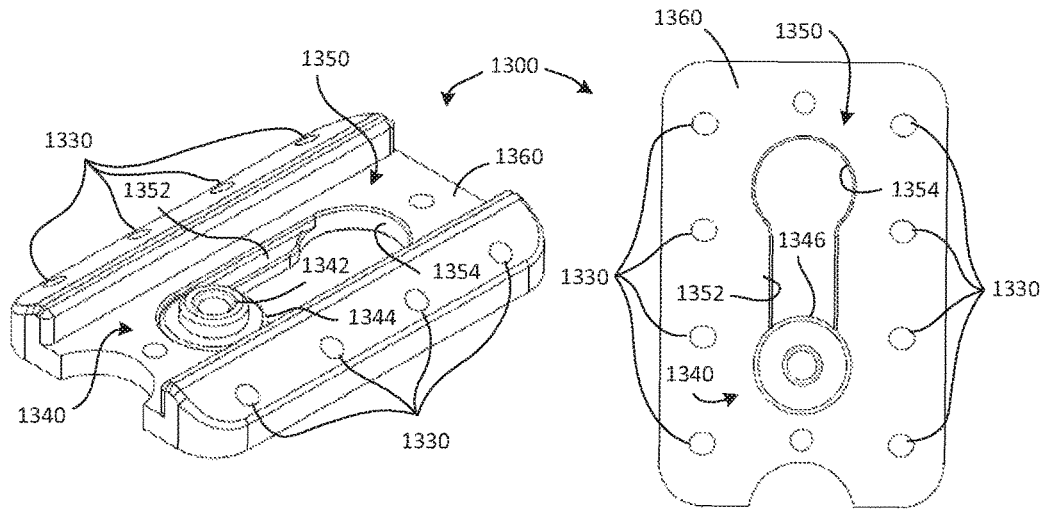
*Fig. 13A*  *Fig. 13B*
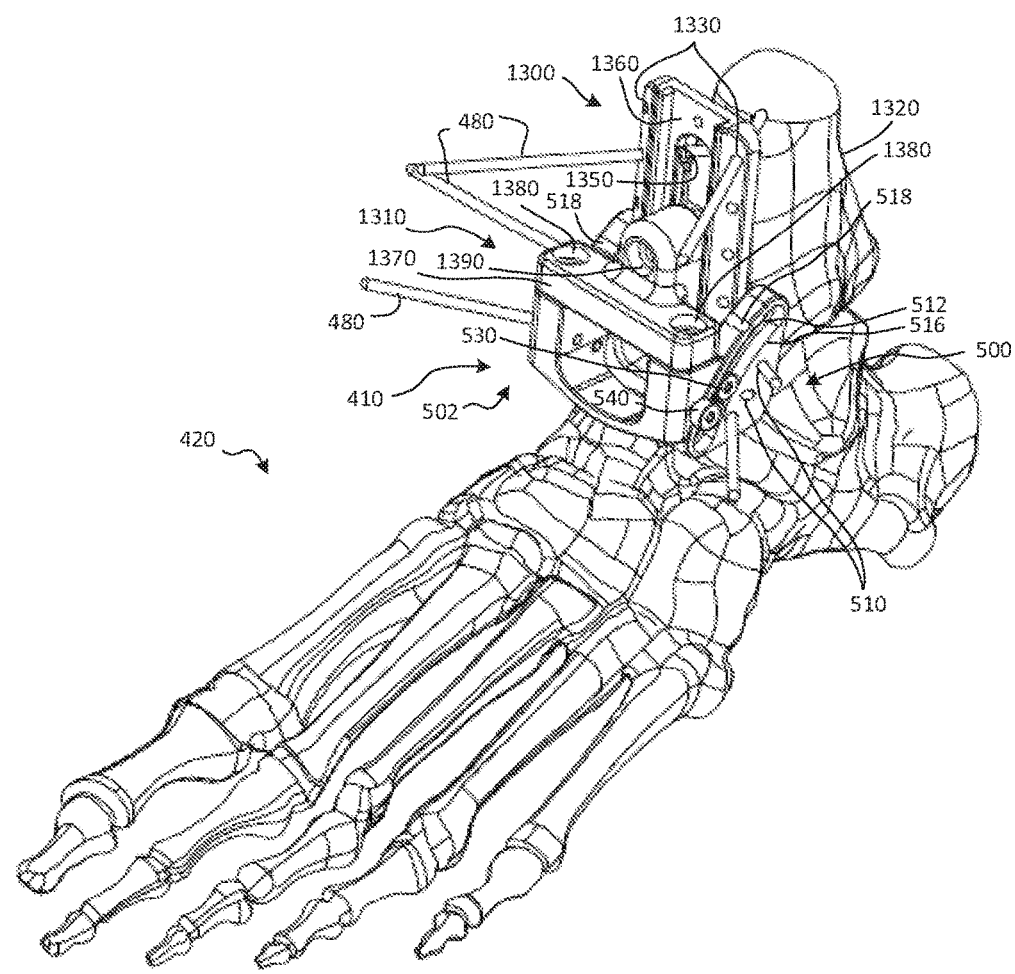
*Fig. 13C*

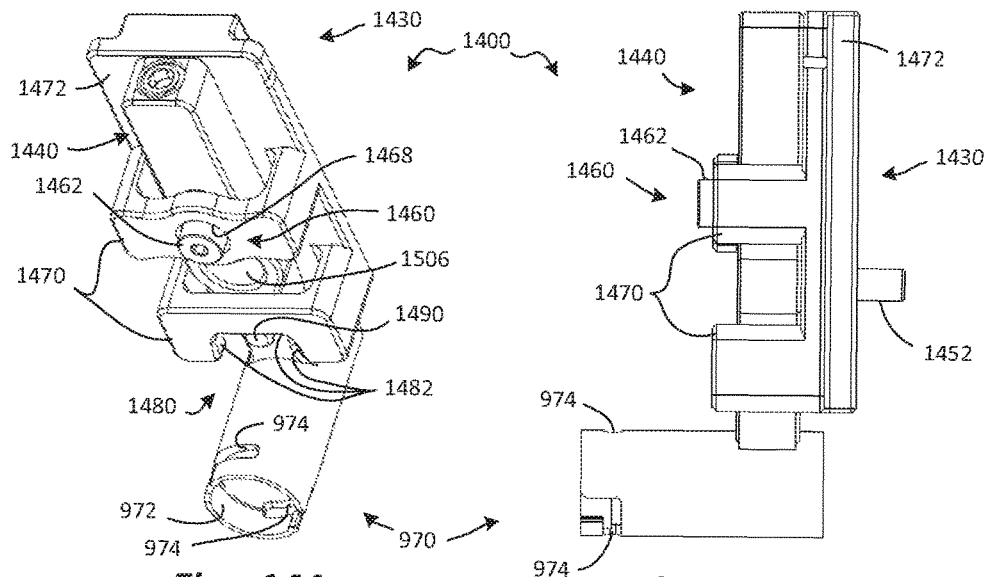
*Fig. 14A*  *Fig. 14B*
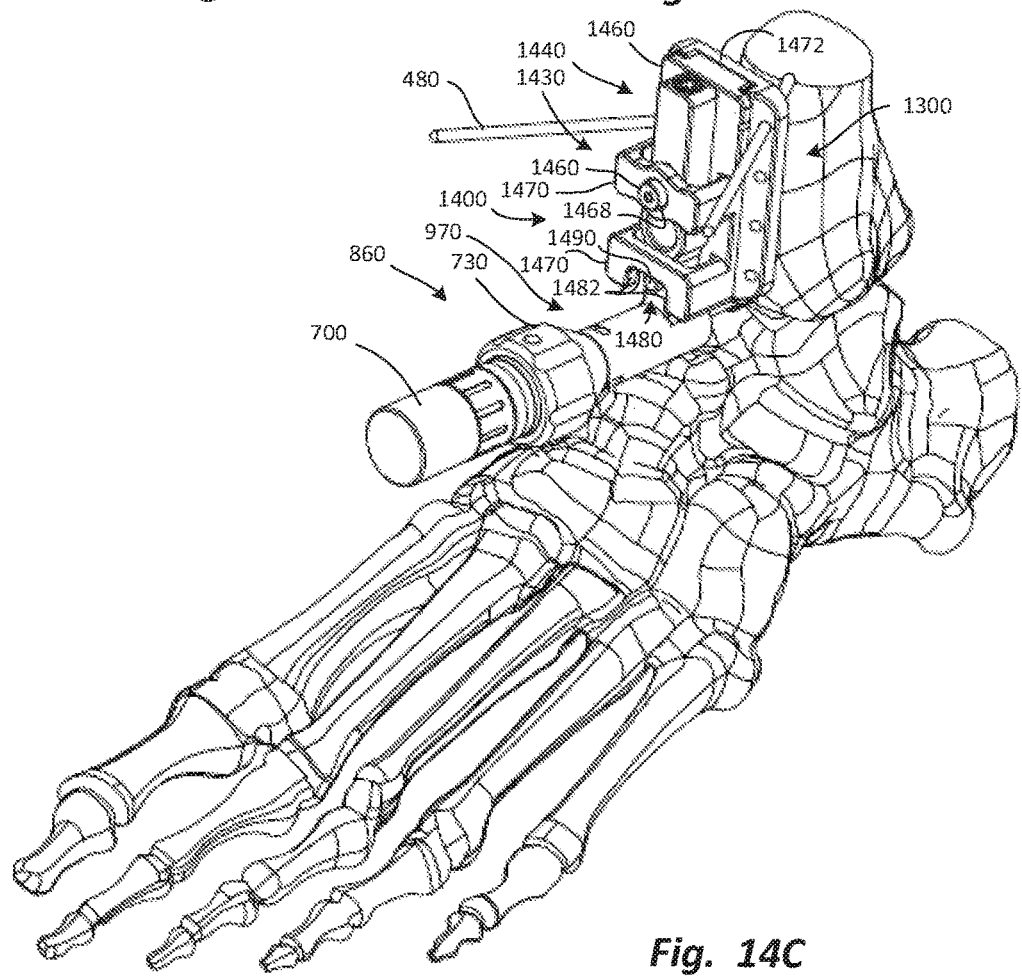
*Fig. 14C*

ANKLE ARTHROPLASTY SYSTEM AND METHODS

TECHNICAL FIELD

The present disclosure relates to surgical systems and methods. More specifically, the present disclosure relates to implants and related methods for ankle arthroplasty.

BACKGROUND

Joint arthroplasty procedures are surgical procedures in which one or more articulating surfaces of a joint are replaced with prosthetic articulating surfaces. Such procedures are becoming increasingly commonplace. Ankle arthroplasty, in particular, may be needed due to trauma or the degeneration of the natural articular surfaces of the tibia and the talus.

For a successful ankle arthroplasty, it is important that the postoperative motion characteristics of the ankle joint mimic, as closely as possible, those of the natural ankle. Further, it is desirable to have the ankle implants remain in place during the subsequent function of the joint. Yet further, it is desirable for the ankle arthroplasty procedure to be carried out quickly and smoothly, with little room for error. Many existing ankle arthroplasty implants and methods are biomechanically inaccurate, are time-consuming to implant, or do not form a sufficient attachment to the underlying bone.

SUMMARY

The various systems and methods of the present disclosure have been developed in response to the present state of the art, and in particular, in response to the problems and needs in the art that have not yet been fully solved by currently available ankle arthroplasty systems and methods. The systems and methods of the present disclosure may provide ankle implants and instruments, including but not limited to talar and tibial prostheses and instruments, that provide enhanced biomechanics, superior bone fixation, and/or streamlined implantation.

According to some embodiments, an ankle arthroplasty system may be designed to replace a natural talar articular surface on a talus and a natural tibial articular surface on a tibia. The ankle arthroplasty system may have a talar prosthesis and a tibial prosthesis, each of which has an articular surface and a bone engagement surface. At least one of the bone engagement surfaces may have a first anterior-posterior curvature and a medial-lateral curvature with a convex shape.

The first anterior-posterior curvature may extend along substantially an entire length, in the anterior-posterior direction, of the bone engagement surface. The bone engagement surface may also have a keel protruding from the first anterior-posterior curvature and extending along the anterior-posterior direction. The keel may have a base portion secured or integrally formed with a remainder of the selection, and a penetrating portion extending from the base portion to penetrate the talar prepared surface or the tibial prepared surface. The penetrating portion may have a generally semicircular perimeter.

The talar articular surface may have two convex talar curvatures extending in the medial-lateral direction, and a concave talar curvature extending in the medial-lateral direction, between the two convex talar curvatures. The tibial articular surface may have two concave tibial curvatures extending in the medial-lateral direction, and a convex tibial curvature extending in the medial-lateral direction, between the two concave tibial curvatures. The talar articular surface and the tibial articular surface may further be shaped such that, with the tibial joint prosthesis centered on the talar joint prosthesis, the two concave tibial curvatures lie substantially flush with the two convex talar curvatures.

The bone engagement surface with the first anterior-posterior curvature may be the talar bone engagement surface, and the first anterior-posterior curvature may be a concave curvature. The talar bone engagement surface may further have a second medial-lateral curvature having a convex shape and extending in the medial-lateral direction, and a central expanse extending in a substantially straight line, along the medial-lateral direction, between the first medial-lateral curvature and the second medial-lateral curvature. The talar bone engagement surface may further have a keel protruding from the first anterior-posterior curvature and extending along the anterior-posterior direction.

The bone engagement surface with the first anterior-posterior curvature may be the tibial bone engagement surface, and the first anterior-posterior curvature may be a convex curvature. The tibial bone engagement surface may further have a second medial-lateral curvature having a convex shape and extending in the medial-lateral direction, and a central expanse extending in a substantially straight line, along the medial-lateral direction, between the first medial-lateral curvature and the second medial-lateral curvature. The tibial bone engagement surface may further have a keel protruding from the first anterior-posterior curvature and extending along the anterior-posterior direction.

According to some embodiments, a talar joint prosthesis may have a talar articular surface shaped to replace a natural talar articular surface, and a talar bone engagement surface shaped to engage a talar prepared surface of a talus. The talar bone engagement surface may have a first anterior-posterior curvature having a concave shape and extending in an anterior-posterior direction, and a first medial-lateral curvature having a convex shape and extending in a medial-lateral direction.

The first anterior-posterior curvature may extend along substantially an entire length, in the anterior-posterior direction, of the talar bone engagement surface. The talar bone engagement surface may further have a second medial-lateral curvature having a convex shape and extending in the medial-lateral direction, and a central expanse extending in a substantially straight line, along the medial-lateral direction, between the first medial-lateral curvature and the second medial-lateral curvature. The talar bone engagement surface may further have a keel protruding from the first anterior-posterior curvature and extending along the anterior-posterior direction. The keel may have a base portion secured or integrally formed with a remainder of the talar bone engagement surface, and a penetrating portion extending from the base portion to penetrate the talar prepared surface. The penetrating portion may have a generally semicircular perimeter.

According to some embodiments, a tibial joint prosthesis may have a tibial articular surface shaped to replace a natural tibial articular surface, and a tibial bone engagement surface shaped to engage a tibial prepared surface of a tibia. The tibial bone engagement surface may have a first anterior-posterior curvature having a convex shape and extending in an anterior-posterior direction, and a first medial-lateral curvature having a convex shape and extending in a medial-lateral direction.

The first anterior-posterior curvature may extend along substantially an entire length, in the anterior-posterior direction, of the tibial bone engagement surface. The tibial bone engagement surface may further have a second medial-lateral curvature having a convex shape and extending in the medial-lateral direction, and a central expanse extending in a substantially straight line, along the medial-lateral direction, between the first medial-lateral curvature and the second medial-lateral curvature. The tibial bone engagement surface may further have a keel protruding from the first anterior-posterior curvature and extending along the anterior-posterior direction. The keel may have a base portion secured or integrally formed with a remainder of the tibial bone engagement surface, and a penetrating portion extending from the base portion to penetrate the tibial prepared surface. The penetrating portion may have a generally semicircular perimeter.

According to some embodiments, system for preparing a bone for joint arthroplasty may have a burr with a rotatable cutting element having a shape, extending along a length of the rotatable cutting element, selected from the group consisting of a concave shape and a convex shape. The system may further have a cutting guide with a bone attachment interface securable to the bone, a burr attachment interface securable to the burr, and a guide mechanism configured to constrain relative motion between the burr attachment interface and the bone attachment interface to facilitate formation of a prepared surface on the bone with the burr. The prepared surface may have at least one concave curvature or one convex curvature.

The cutting guide may further have a foundation and a burr holder. The foundation may have the bone attachment interface and a burr holder interface. The burr holder may have the burr attachment interface and a foundation interface that can be coupled to the burr holder interface.

The guide mechanism may permit motion of the burr attachment interface along a first direction perpendicular to the length of the rotatable cutting element. The guide mechanism may guide motion of the burr attachment interface along a straight line perpendicular to the length of the rotatable cutting element. The shape of the rotatable cutting element may be a convex shape with a maximum radius perpendicular to the length, such that the prepared surface has a cross-sectional shape with a first convex curvature with a first curvature radius substantially equal to the maximum radius, a second convex curvature with a second curvature radius substantially equal to the maximum radius, and a central expanse extending in a substantially straight line between the first convex curvature and the second convex curvature.

The guide mechanism may further permit motion of the burr attachment interface along a second direction parallel to the length of the rotatable cutting element. The guide mechanism may permit motion of the burr attachment interface along the second direction by permitting rotation of the burr attachment interface about an axis perpendicular to the rotatable cutting element. The shape of the rotatable cutting element may be a concave shape with a maximum radius perpendicular to the length, such that the prepared surface has a cross-sectional shape with a first convex curvature with a first curvature radius substantially equal to the maximum radius, a second convex curvature with a second curvature radius substantially equal to the maximum radius, and a central expanse extending in a substantially straight line between the first convex curvature and the second convex curvature. The cross-sectional shape may be swept along a convex curvature.

According to some embodiments, a method for preparing a bone for joint arthroplasty may include positioning a cutting guide proximate the bone; the cutting guide may include a bone attachment interface, a burr attachment interface, and a guide mechanism. The method may further include securing the bone attachment interface to the bone and securing a burr to the burr attachment interface. The burr may have a rotatable cutting element with a shape, extending along a length of the rotatable cutting element, selected from the group consisting of a concave shape and a convex shape. The method may further include, with the guide mechanism, guiding motion of the burr relative to the bone to facilitate formation of a prepared surface on the bone with the burr. The prepared surface may have at least one concave curvature or one convex curvature.

The cutting guide may further have a foundation with the bone attachment interface and a burr holder interface. Further, the cutting guide may have a burr holder with the burr attachment interface and a foundation interface. The method may further include coupling the foundation interface of the burr holder to the burr holder interface of the foundation.

Guiding motion of the burr relative to the bone may include, with the guide mechanism, permitting motion of the burr along a first direction perpendicular to the length of the rotatable cutting element. Guiding motion of the burr relative to the bone may further include, with the guide mechanism, guiding motion of the burr attachment interface along a straight line perpendicular to the length of the rotatable cutting element. The shape may be a convex shape with a maximum radius perpendicular to the length, such that the prepared surface has a cross-sectional shape with a first convex curvature with a first curvature radius substantially equal to the maximum radius, a second convex curvature with a second curvature radius substantially equal to the maximum radius, and a central expanse extending in a substantially straight line between the first convex curvature and the second convex curvature.

Guiding motion of the burr relative to the bone may further include permitting motion of the burr attachment interface along a second direction parallel to the length of the rotatable cutting element. Guiding motion of the burr relative to the bone may further include permitting rotation of the burr attachment interface about an axis perpendicular to the rotatable cutting element. The shape may be a concave shape with a maximum radius perpendicular to the length, such that the prepared surface has a cross-sectional shape with a first convex curvature with a first curvature radius substantially equal to the maximum radius, a second convex curvature with a second curvature radius substantially equal to the maximum radius, and a central expanse extending in a substantially straight line between the first convex curvature and the second convex curvature. The cross-sectional shape may be swept along a convex curvature.

According to some embodiments, a system for preparing a talus or a tibia for ankle arthroplasty may include a first burr and a first cutting guide. The first burr may have a first rotatable cutting element having a first shape, extending along a length of the first rotatable cutting element. The first shape may be selected from the group consisting of a concave shape and a convex shape. The first cutting guide may include a first bone attachment interface securable to the talus or the tibia, a first burr attachment interface securable to the first burr, and a first guide mechanism configured to constrain relative motion between the first burr attachment interface and the first bone attachment interface by permitting motion of the first burr attachment interface along a first direction perpendicular to a first length of the first rotatable cutting element to facilitate formation of a first prepared surface on the tibia or the talus with the first burr. The first prepared surface may have at least one concave curvature or one convex curvature.

The first bone attachment interface may be securable to the talus such that the first prepared surface is on the talus. The first guide mechanism may further permit motion of the first burr attachment interface along a second direction, parallel to the first length of the first rotatable cutting element, by permitting rotation of the first burr attachment interface about an axis perpendicular to the first rotatable cutting element. The first shape may be a concave shape such that the first prepared surface has a cross-sectional shape swept along a convex curvature.

The system may further include a second burr with a second rotatable cutting element having a convex shape, and a second cutting guide. The second cutting guide may have a second bone attachment interface securable to the tibia, a second burr attachment interface securable to the second burr, and a second guide mechanism configured to constrain relative motion between the second burr attachment interface and the second bone attachment interface by permitting motion of the second burr attachment interface along a third direction perpendicular to a second length of the second rotatable cutting element to facilitate formation of a second prepared surface on the tibia with the second burr. The second prepared surface may have at least one concave curvature.

The first cutting guide may further have a first foundation with the first bone attachment interface and a first burr holder. The first foundation may further have a first burr holder interface. The first burr holder may have the first burr attachment interface, and a first foundation interface that can be coupled to the first burr holder interface. The second cutting guide may further have a second foundation and a second burr holder. The second foundation may have the second bone attachment interface and a second burr holder interface. The second burr holder may have the second burr attachment interface, and a second foundation interface that can be coupled to the second burr holder interface. The system may further include an alignment block with a third foundation interface attachable to the first foundation, and a fourth foundation interface attachable to the second foundation to facilitate positioning of the second foundation relative to the first foundation.

According to some embodiments, a method for performing ankle arthroplasty may include exposing an anterior aspect of the ankle joint, securing a first cutting guide to a first bone that is the talus or the tibia, inserting a first cutting tool into the ankle joint from along an anterior approach, and using the first cutting guide to guide motion of the first cutting tool relative to the first bone to cause the first cutting tool to form a first prepared surface on the first bone. The first prepared surface may have a first anterior-posterior curvature extending anterior-posteriorly. The method may further include placing a first prosthesis on the first prepared surface. The first prosthesis may have a first articular surface shaped to replace a first natural articular surface of the first bone.

The first prosthesis may have a keel. The method may further include inserting a second cutting tool into the ankle joint from along an anterior approach, and, with the first cutting guide, guiding motion of the second cutting tool relative to the first bone to cause the second cutting tool to form a slot in the first bone such that the slot is oriented anterior-posteriorly. Placing the first prosthesis on the first prepared surface may include inserting the keel into the slot.

The first bone may be the tibia. The first anterior-posterior curvature may be a concave curvature extending anterior-posteriorly. The first prosthesis may have a convex bone engagement surface. Placing the first prosthesis on the first prepared surface may include inserting the convex bone engagement surface into the concave curvature.

The first bone may be the talus. The first anterior-posterior curvature may be a convex curvature extending anterior-posteriorly. The first prosthesis may have a concave bone engagement surface. Placing the first prosthesis on the first prepared surface may include positioning the convex curvature in the concave bone engagement surface.

The method may further include exposing an anterior aspect of the ankle joint, securing a second cutting guide to the tibia, and inserting the first cutting tool or a second cutting tool into the ankle joint from along an anterior approach. Further, the method may include, with the second cutting guide, guiding motion of the first cutting tool or the second cutting tool relative to the tibia to cause the first cutting tool or the second cutting tool to form a second prepared surface on the tibia such that the second prepared surface has a second anterior-posterior curvature with a concave curvature extending anterior-posteriorly. The method may further include placing a second prosthesis on the second prepared surface. The second prosthesis may have a convex bone engagement surface, and a second articular surface shaped to replace a second natural articular surface of the tibia. Placing the second prosthesis on the second prepared surface may include inserting the convex bone engagement surface into the concave curvature.

The first cutting guide may have a talar foundation with a talar bone attachment interface and a talar tool holder interface, and a talar tool holder with a talar tool attachment interface and a talar foundation interface. Securing the first cutting guide to the first bone may include securing the talar bone attachment interface to the talus. The method may further include, prior to guiding motion of the first cutting tool with the first cutting guide, coupling the talar foundation to the talar tool holder by coupling the talar tool holder interface to the talar foundation interface, and attaching the first cutting tool to the talar tool attachment interface.

The method may further include, prior to securing the talar foundation to the talus, positioning a trial on the talus. The trial may be coupled to a distal end of a column. The method may further include, prior to securing the talar foundation to the talus, using the column to align the trial with the talus by aligning a proximal end of the column with a landmark on portion of a patient's leg proximal to the talus, and aligning the talar foundation with the trial.

The method may further include attaching a talar foundation interface of an alignment block to the talar foundation, and attaching a tibial foundation interface of the alignment block to a tibial foundation. The tibial foundation may have a tibial bone attachment interface and a tibial tool holder interface. The method may further include securing the tibial bone attachment interface to the tibia, and coupling a tibial tool holder to the tibial foundation by coupling the tibial tool holder interface to a tibial foundation interface of the tibial tool holder. The tibial foundation and the tibial tool holder may constitute a second cutting guide.

The method may further include attaching the first cutting tool or a second cutting tool to a tibial tool attachment interface of the tibial tool holder, inserting the first cutting tool or the second cutting tool into the ankle joint from along an anterior approach, and, with the second cutting guide, guiding motion of the first cutting tool or the second cutting tool relative to the tibia in a medial-lateral direction to cause the first cutting tool or the second cutting tool to form a second prepared surface on the tibia. The second prepared surface may have a second anterior-posterior curvature with a concave curvature extending anterior-posteriorly.

Guiding motion of the first cutting tool relative to the first bone to form the first prepared surface may include moving the first cutting tool in a medial-lateral direction. Guiding motion of the first cutting tool relative to the first bone to form the first prepared surface may further include rotating the first cutting tool relative to the first bone about an axis extending medial-laterally to cause the first cutting tool to move anterior-posteriorly.

According to some embodiments, a method for performing ankle arthroplasty on an ankle joint with a talus and a tibia may include exposing an anterior aspect of the ankle joint, securing a talar cutting guide to the talus, and inserting a first cutting tool into the ankle joint from along an anterior approach. The method may further include, with the talar cutting guide, guiding motion of the first cutting tool relative to the talus to rotate the first cutting tool relative to the talus about an axis extending medial-laterally to cause the first cutting tool to move anterior-posteriorly to form a first prepared surface on the talus. The first prepared surface may have a first anterior-posterior curvature extending anterior-posteriorly. The method may further include placing a talar prosthesis on the first prepared surface. The talar prosthesis may have a talar articular surface shaped to replace a natural talar articular surface of the talus.

The talar prosthesis may have a keel. The method may further include inserting the first cutting tool or a second cutting tool into the ankle joint from along an anterior approach, and, with the talar cutting guide, guiding motion of the first cutting tool or the second cutting tool relative to the talus to cause the first cutting tool or the second cutting tool to form a slot in the talus such that the slot is oriented anterior-posteriorly. Placing the talar prosthesis on the first prepared surface may include inserting the keel into the slot.

Guiding motion of the first cutting tool relative to the talus to form the first prepared surface may further include moving the first cutting tool in a medial-lateral direction. The method may further include securing a tibial cutting guide to the tibia and inserting the first cutting tool or a second cutting tool into the ankle joint from along an anterior approach. The method may further include, with the tibial cutting guide, guiding motion of the first cutting tool relative to the tibia to move the first cutting tool or a second cutting tool medial-laterally to form a second prepared surface on the tibia. The second prepared surface may have a second anterior-posterior curvature extending anterior-posteriorly. The method may further include placing a tibial prosthesis on the second prepared surface. The tibial prosthesis may have a tibial articular surface shaped to replace a natural tibial articular surface of the tibia.

The talar cutting guide may have a talar foundation and a talar tool holder. The talar foundation may have a talar bone attachment interface and a talar tool holder interface. The talar tool holder may have a talar tool attachment interface and a talar foundation interface. Securing the talar cutting guide to the talus may include securing the talar bone attachment interface to the talus. The method may further include, prior to guiding motion of the first cutting tool with the talar cutting guide, coupling the talar foundation to the talar tool holder by coupling the talar tool holder interface to the talar foundation interface, and attaching the first cutting tool to the talar tool attachment interface.

The method may further include attaching a talar foundation interface of an alignment block to the talar foundation and attaching a tibial foundation interface of the alignment block to a tibial foundation. The tibial foundation may have a tibial bone attachment interface and a tibial tool holder interface. The method may further include securing the tibial bone attachment interface to the tibia, and coupling a tibial tool holder to the tibial foundation by coupling the tibial tool holder interface to a tibial foundation interface of the tibial tool holder. The tibial foundation and the tibial tool holder may constitute a second cutting guide.

According to some embodiments, a method for performing ankle arthroplasty on an ankle joint with a talus and a tibia may include exposing an anterior aspect of the ankle joint, securing a talar cutting guide to the talus, inserting a first cutting tool into the ankle joint from along an anterior approach, and, with the talar cutting guide, guiding motion of the first cutting tool relative to the talus to cause the first cutting tool to form a first prepared surface on the talus. The first prepared surface may have a first anterior-posterior curvature extending anterior-posteriorly. The method may further include securing a tibial cutting guide to the tibia, inserting the first cutting tool or a second cutting tool into the ankle joint from along the anterior approach, and, with the tibial cutting guide, guiding motion of the first cutting tool or the second cutting tool relative to the tibia to cause the first cutting tool or the second cutting tool to form a second prepared surface on the tibia. The second prepared surface may have a second anterior-posterior curvature extending anterior-posteriorly. The method may further include placing a talar prosthesis on the first prepared surface, and placing a tibial prosthesis on the second prepared surface. The talar prosthesis may have a talar articular surface shaped to replace a first natural articular surface of the talus, and the tibial prosthesis may have a tibial articular surface shaped to replace a second natural articular surface of the tibia.

The talar prosthesis may have a talar keel, and the tibial prosthesis may have a tibial keel. The method may further include, with the talar cutting guide, guiding motion of the first cutting tool, the second cutting tool, or a third cutting tool relative to the talus to form a first slot in the talus such that the first slot is oriented anterior-posteriorly. The method may further include, with the tibial cutting guide, guiding motion of the first cutting tool, the second cutting tool, the third cutting tool, or a fourth cutting tool relative to the tibia to form a second slot in the tibia, such that the second slot is oriented anterior-posteriorly. Placing the talar prosthesis on the first prepared surface may include inserting the talar keel into the first slot. Placing the tibial prosthesis on the second prepared surface may include inserting the tibial keel into the second slot.

The talar cutting guide may include a talar foundation and a talar tool holder. The tibial cutting guide may have a tibial foundation and a tibial tool holder. Securing the talar cutting guide to the talus may include securing the talar foundation to the talus. The method may further include, prior to guiding motion of the first cutting tool or the second cutting tool with the tibial cutting guide, attaching a talar foundation interface of an alignment block to the talar foundation, and attaching a tibial foundation interface of the alignment block to the tibial foundation. Securing the tibial cutting guide to the tibia may include securing the tibial foundation to the tibia with the talar foundation interface attached to the talar foundation and the tibial foundation interface attached to the tibial foundation.

According to some embodiments, a system for preparing a bone for joint arthroplasty may have a cutting tool and a guide assembly securable to the bone. The guide assembly may have a base and an arm. The base may have a first coupling feature and a first guide feature. The arm may have a second coupling feature movably coupled to the first coupling feature, a tool attachment interface attachable to the cutting tool, and a second guide feature. One of the first guide feature and the second guide feature may have a guide surface having a predetermined shape. The other of the first guide feature and the second guide feature may include a follower configured to slide along the guide surface to constrain motion of the tool attachment interface relative to the base.

The first coupling feature and the second coupling feature may be coupled together to permit the arm to rotate relative to the base about an arm rotation axis. The guide surface may face either toward the arm rotation axis, or away from the arm rotation axis. The guide surface may have a planar shape configured to prevent motion of a cutting tool axis of the cutting tool beyond a planar boundary to prevent excessive penetration of the bone by the cutting tool. The cutting tool may include a burr with a cutting element that rotates about the cutting tool axis.

The guide surface may be on the base and the follower may be on the arm. The follower may include a cylindrical post protruding from a remainder of the arm.

The arm may include a first arm member having at least part of the second coupling feature, and a second arm member, slidably coupled to the first arm member, having the tool attachment interface and the second guide feature. The system may further include a resilient member that urges the follower toward the guide surface and urges the cutting tool toward the bone.

The guide assembly may further have a foundation with a bone attachment interface attachable to the bone, and a base attachment interface attachable to a foundation attachment interface of the base. The foundation may further have a stationary member having the bone attachment interface, and a mobile member coupled to the stationary member such that the mobile member is rotatable relative to the stationary member about a foundation axis perpendicular to the arm rotation axis. The mobile member may have the base attachment interface.

The bone may be a talus or a tibia. The bone attachment interface may be configured to attach the foundation to the talus or to the tibia, proximate an ankle joint defined by the talus and the tibia.

According to some embodiments, a method for preparing a bone for joint arthroplasty may include securing a guide assembly to a bone. The guide assembly may include a base and an arm. The base may include a first coupling feature and a first guide feature. The arm may include a second coupling feature movably coupled to the first coupling feature, a tool attachment interface, and a second guide feature. The method may further include attaching a cutting tool to the tool attachment interface, and moving the arm relative to the base to guide motion of the cutting tool relative to the bone to cause the cutting tool to form a prepared surface on the bone. One of the first guide feature and the second guide feature may include a guide surface with a predetermined shape. The other of the first guide feature and the second guide feature may include a follower. Moving the arm relative to the base may include sliding the follower along the guide surface to constrain motion of the tool attachment interface relative to the base.

Moving the arm relative to the base may further include rotating the arm relative to the base about an arm rotation axis. The guide surface may face either toward the arm rotation axis, or away from the arm rotation axis.

The guide surface may have a planar shape. The cutting tool may include a burr with a cutting element that rotates about a cutting tool axis. Sliding the follower along the guide surface to constrain motion of the tool attachment interface relative to the base may include preventing motion of the cutting tool axis beyond a planar boundary to prevent excessive penetration of the bone by the burr.

The arm may include a first arm member having at least part of the second coupling feature, and a second arm member, slidably coupled to the first arm member, having the tool attachment interface and the second guide feature. Sliding the follower along the guide surface to constrain motion of the tool attachment interface relative to the base may include siding the second arm member relative to the first arm member. The guide assembly may further include a resilient member. Sliding the follower along the guide surface to constrain motion of the tool attachment interface relative to the base further may further include, with the resilient member, urging the follower toward the guide surface and urging the cutting tool toward the bone.

The guide assembly may further include a foundation with a stationary member having a bone attachment interface, and a mobile member rotatably coupled to the stationary member. The mobile member may have a base attachment interface. Securing the guide assembly to the bone may include attaching the bone attachment interface to a talus. The method may further include, prior to moving the arm relative to the base to guide motion of the cutting tool relative to the bone, attaching a foundation attachment interface of the base to the base attachment interface. Moving the arm relative to the base to guide motion of the cutting tool relative to the bone further may include rotating the mobile member relative to the stationary member about a foundation axis.

The guide assembly may further have a foundation with a bone attachment interface and a base attachment interface. Securing the guide assembly to the bone may include attaching the bone attachment interface to a tibia. The method may further include, prior to moving the arm relative to the base to guide motion of the cutting tool relative to the bone, attaching a foundation attachment interface of the base to the base attachment interface.

According to some embodiments, a system for preparing a talus or a tibia for ankle arthroplasty may include a burr with a cutting element that rotates about a burr axis, and a guide assembly securable to the talus or the tibia. The guide assembly may have a base with a first coupling feature, a first guide feature, and an arm. The arm may have a first arm member with at least part of a second coupling feature coupled to the first coupling feature to permit the arm to rotate relative to the base about an arm rotation axis. The arm may also have a second arm member slidably coupled to the first arm member. The second arm member may have a tool attachment interface attachable to the burr, a second guide feature, and a resilient member. One of the first guide feature and the second guide feature may include a guide surface having a planar shape configured to prevent motion of the burr axis beyond a planar boundary to prevent excessive penetration of the talus or the tibia by the burr. The other of the first guide feature and the second guide feature may include a follower configured to slide along the guide surface to constrain motion of the tool attachment interface relative to the base. The resilient member may urge the follower toward the guide surface and may urge the burr toward the talus or the tibia.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIGS. 2A through 2E are cephalad perspective, caudal perspective, side elevation, lateral section, and anterior section views, respectively, of the talar prosthesis.

FIGS. 3A through 3E are cephalad perspective, caudal perspective, side elevation, lateral section, and anterior section views, respectively, of the tibial prosthesis.

FIGS. 4A through 4C are cephalad perspective, caudal perspective, and cephalad perspective views, respectively, of a trial that may be used to position a talar foundation relative to a talus through the use of a column, with the talar foundation and the column assembled with the talus and the trial in FIG. 4C.

FIGS. 5A, 5B, and 5C are posterior cephalad perspective, anterior cephalad perspective, and anterior cephalad perspective views, respectively, of the talar foundation of FIG. 4C, with the talar foundation fixed to the talus in FIG. 5C.

FIGS. 9A through 9C are cephalad perspective caudal perspective, and anterior elevation, section views, respectively, of the talar burr holder of FIGS. 6A and 6B.

FIGS. 13A through 13C are posterior caudal perspective, anterior elevation, and anterior cephalad perspective views, respectively, of a tibial foundation, with an alignment block and talar foundation also depicted in FIG. 13C to secure the tibial foundation to a tibia.

FIGS. 14A, 14B, and 14C are anterior cephalad perspective, lateral elevation, and anterior cephalad perspective views, respectively, of a tibial burr holder, with the tibial burr holder secured to the tibial foundation and the tibia in FIG. 14C.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 16, is not intended to limit the scope of the claims, as claimed, but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1A:
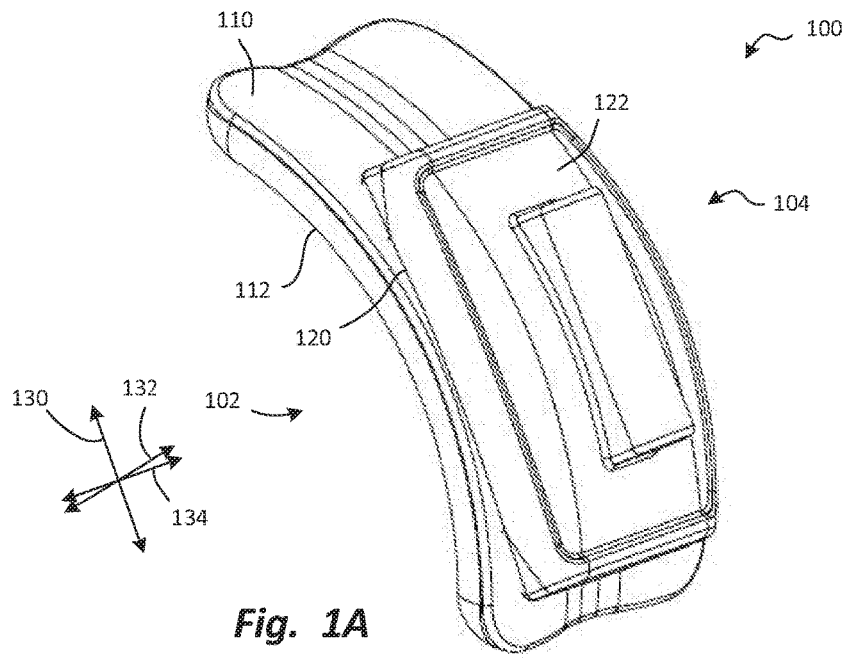
FIGS. 1A, 1B, and 1C are cephalad perspective, side elevation, and anterior section views, respectively, of an ankle arthroplasty system according to one embodiment.
Figure 1B:
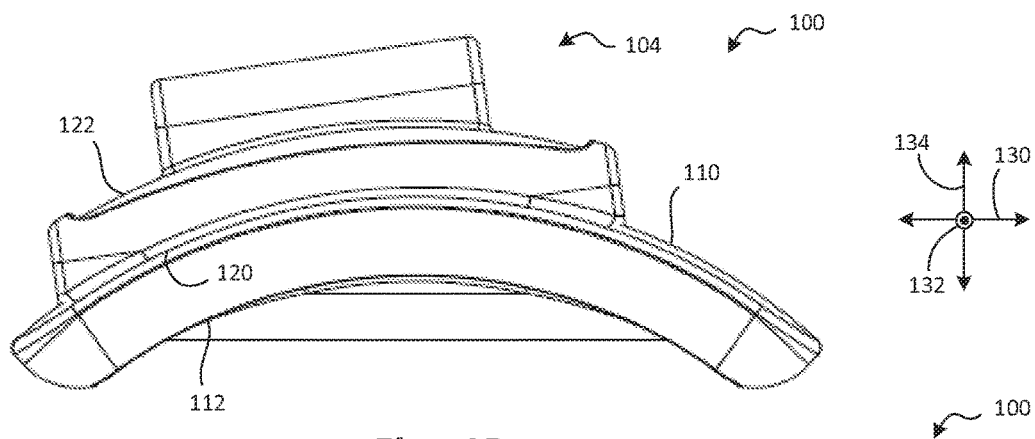
Figure 1C:
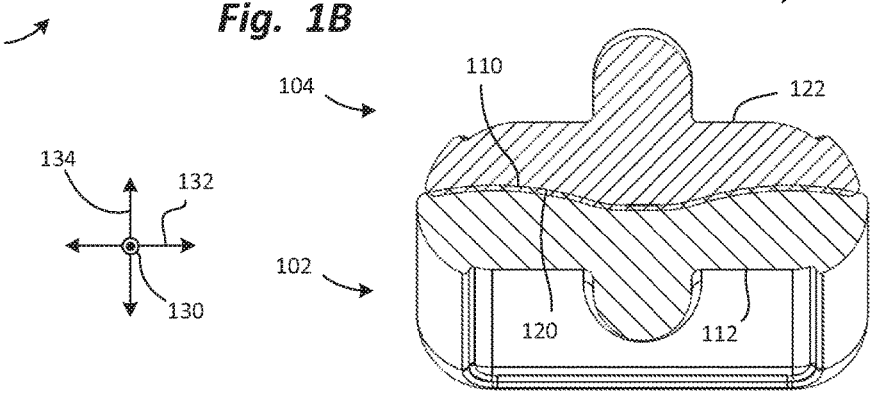

FIGS. 1A, 1B, and 1C are perspective, lateral elevation, and anterior section views, respectively, of an ankle arthroplasty system, or system 100, according to one embodiment. The system 100 may be designed to replace the natural articulating surfaces of an ankle joint, and may thus have a talar prosthesis 102 and a tibial prosthesis 104. In some embodiments, the u system 100 may be designed to replace only the talar or tibial articulating surfaces, and may thus include only the talar prosthesis 102 or the tibial prosthesis 104.

The talar prosthesis 102 and the tibial prosthesis 104 may each have an articular surface and a bone engagement surface. Specifically, the talar prosthesis 102 may have a talar articular surface 110 shaped to replace the natural articular surface of a talus, and a talar bone engagement surface 112 shaped to engage a talar prepared surface of a talus either by direct contact if the talar bone engagement surface 112 is of a porous in-growth material, or through a layer of an adhesive such as poly-methacrylate (PMMA, or "bone cement"). Similarly, the tibial prosthesis 104 may have a tibial articular surface 120 shaped to replace the natural articular surface of a tibia, and a tibial bone engagement surface 122 shaped to engage a tibial prepared surface of a tibia either by direct contact if the talar bone engagement surface 122 is of a porous in-growth material, or through a layer of an adhesive such as PMMA.

The system 100 is shown relative to directions applicable when the system 100 is implanted in an ankle joint. These directions may include an anterior-posterior direction 130, a medial-lateral direction 132, and a cephalad-caudal direction 134. In this application, these directions may be referred to as, for example, "in the anterior-posterior direction 130," or "anterior-posteriorly." Directions may refer to motion of an object; for example, an object that moves in the anterior-posterior direction 130 moves in the anterior direction and/or the posterior direction. In the alternative, directions may refer to the orientation of an object or feature. For example, an object or feature that extends anterior-posteriorly is oriented such that its greatest length is generally parallel to the anterior-posterior direction 130.

The talar prosthesis 102 will be shown and described in greater detail in connection with FIGS. 2A through 2E. The tibial prosthesis 104 will be shown and described in greater detail in connection with FIGS. 3A through 3E.

FIGS. 2A through 2E are cephalad perspective, caudal perspective, side elevation, lateral section, and anterior section views, respectively, of the talar prosthesis 102. The talar articular surface 110 may be shaped to mimic the shape of the natural talar articular surface. In some embodiments, the talar articular surface 110 may have two convex talar curvatures 200 extending medial-laterally. The convex talar curvatures 200 may be separated from each other by a concave talar curvature 202 extending medial-laterally. The convex talar curvatures 200 and the concave talar curvature 202 are most easily seen in FIG. 2E, in which the section plane extends medial-laterally and cephalad-caudally, parallel to the convex talar curvatures 200 and the concave talar curvature 202.

The talar bone engagement surface 112 may be shaped to provide secure engagement, using either a porous bone in-growth surface or a surface adapted for bone cement, with a prepared surface of a talus, which will be shown and described subsequently. In some embodiments, the talar bone engagement surface 112 may have a main portion 210 and a keel 212 extending from the main portion 210. The main portion 210 may have contouring that helps it remain securely seated on the talus, while leaving much of the adjacent bone of the talus intact. Thus, the talar prosthesis 102 may be a "bone sparing" prosthesis.

In some embodiments, the main portion 210 may have two medial-lateral curvatures 220 positioned at the edges of the talar bone engagement surface 112, and a central expanse 222 that extends substantially straight, medial-laterally, between the two medial-lateral curvatures 220. The medial-lateral curvatures 220 and the central expanse 222 are most easily seen in FIG. 2E, in which the section plane extends medial-laterally and cephalad-caudally, parallel to the medial-lateral curvatures 220 and the central expanse 222. The central expanse 222 may optionally be slightly recessed relative to the medial-lateral curvatures 220, defining a wall 224 facing toward the keel 212. The circumferential wall 224 may act as a retaining wall for the bone cement when the talar prosthesis 102 is implanted. If the talar prosthesis 102 is to be fixed to the bone using a porous interface, then the wall 224 may be used to contain the porous material.

The main portion 210 may also have an anterior-posterior curvature 230 extending anterior-posteriorly. Thus, the cross-sectional shape of the main portion 210 may be generally arcuate, with a concave shape, when viewed from a lateral viewpoint, as in FIG. 2C, and may be generally rectilinear when viewed from an anterior viewpoint, as in FIG. 2E. The main portion 210 may be described as the surface formed when the cross-sectional shape defined by the medial-lateral curvatures 220, the central expanse 222, and optionally, the wall 224, as shown in FIG. 2E, is swept along the arcuate pathway of the anterior-posterior curvature 230. Similarly, the talar articular surface 110 may be described as the surface formed when the cross-sectional shape defined by the medial-lateral curvatures 220 and the anterior-posterior curvature 230, as also shown in FIG. 2E, is swept along a similar arcuate pathway.

The keel 212 may also have a bone-sparing shape. Specifically, the keel 212 may have a base portion 240 that is integrally formed with the remainder of the talar prosthesis 102, and a penetrating portion 242 extending from the base portion 240 to penetrate the bone of the talus. The penetrating portion 242 may have, at its cephalad end, a generally semicircular perimeter 244. The generally semicircular perimeter 244 may help to preserve bone by presenting medially and laterally-facing surface areas that resist motion of the talar prosthesis 102 medially or laterally, relative to the bone. The resistance to medial or lateral motion may be equal to that provided by a keel with a rectangular cross-sectional shape, without requiring removal of as much bone as a rectangular perimeter.

In some alternative embodiments (not shown), fixation pegs may be used in addition to or in place of the keel 212. Such fixation pegs may have any size or shape known in the art. In some embodiments, the fixation pegs may be permanently secured to the remainder of the talar bone engagement surface 112. In other embodiments, the fixation pegs may be modular, and may be attached, for example, to receiving features in the bone engagement surface, such as mounting apertures. In yet other embodiments, the fixation pegs may be deployable in-situ, and may be movable from retracted to deployed positions to facilitate placement of the talar prosthesis and/or reduce the amount of distraction of the ankle joint that is required for implantation.

FIGS. 3A through 3E are cephalad perspective, caudal perspective, side elevation, lateral section, and anterior section views, respectively, of the tibial prosthesis 104. The tibial articular surface 120 may be shaped to mimic the shape of the natural tibial articular surface. In some embodiments, the tibial articular surface 120 may have two concave tibial curvatures 300 extending medial-laterally. The concave tibial curvatures 300 may be separated from each other by a convex tibial curvature 302 extending medial-laterally. The concave tibial curvatures 300 and the convex tibial curvature 302 are most easily seen in FIG. 3E, in which the section plane extends medial-laterally and cephalad-caudally, parallel to the concave tibial curvatures 300 and the convex tibial curvature 302.

In a centered position of the ankle joint after arthroplasty is complete, the convex talar curvatures 200 of the talar prosthesis 102 may reside in the concave tibial curvatures 300 of the tibial prosthesis 104, and the convex tibial curvature 302 of the tibial prosthesis 104 may rest in the concave talar curvature 202 of the talar prosthesis 102. This is the arrangement depicted in FIG. 1C. As the tibia rotates medially or laterally relative to the talus, one of the concave tibial curvatures 300 may slide along the adjacent one of the convex talar curvatures 200 so that the other of the concave tibial curvatures 300 is displaced from the adjacent one of the convex talar curvatures 200. The configuration and operation of the talar articular surface 110 and the tibial articular surface 120 set forth herein are merely exemplary; in alternative embodiments, any arrangement of articular surfaces and motion pathways known in the art may be used.

The tibial bone engagement surface 122 may be shaped to provide secure engagement with a prepared surface of a tibia, which will be shown and described subsequently. In some embodiments, the tibial bone engagement surface 122 may have a main portion 310 and a keel 312 extending from the main portion 310. The main portion 310 may have contouring that helps it remain securely seated on the tibia, while leaving much of the adjacent bone of the tibia intact. Thus, the tibial prosthesis 104 may be a "bone sparing" prosthesis.

In some embodiments, the main portion 310 may have two medial-lateral curvatures 320 positioned at the edges of the tibial bone engagement surface 122, and a central expanse 322 that extends substantially straight, medial-laterally, between the two medial-lateral curvatures 320. The medial-lateral curvatures 320 and the central expanse 322 are most easily seen in FIG. 3E, in which the section plane extends medial-laterally and cephalad-caudally, parallel to the medial-lateral curvatures 320 and the central expanse 322. The central expanse 322 may optionally be slightly recessed relative to the medial-lateral curvatures 320, defining a wall 324 facing toward the keel 312. The circumferential wall 324 may act as a retaining wall for bone cement during implantation of the tibial prosthesis 104. If the tibial component is to be fixed to the bone using a porous interface, then the wall 324 may be used to contain the porous material.

The main portion 310 may also have an anterior-posterior curvature 330 extending anterior-posteriorly. Thus, the cross-sectional shape of the main portion 310 may be generally arcuate, with a convex shape, when viewed from a lateral viewpoint, as in FIG. 3C, and may be generally rectilinear when viewed from an anterior viewpoint, as in FIG. 3E. The main portion 310 may be described as the surface formed when the cross-sectional shape defined by the medial-lateral curvatures 320, the central expanse 322, and optionally, the wall 324, as shown in FIG. 3E, is swept along the arcuate pathway of the anterior-posterior curvature 330. Similarly, the tibial articular surface 120 may be described as the surface formed when the cross-sectional shape defined by the medial-lateral curvatures 320 and the central expanse 322, as also shown in FIG. 2E, is swept along a similar arcuate pathway.

The keel 312 may also have a bone-sparing shape similar to that of the keel 212. Specifically, the keel 312 may have a base portion 340 that is integrally formed with the remainder of the tibial prosthesis 104, and a penetrating portion 342 extending from the base portion 340 to penetrate the bone of the talus. The penetrating portion 342 may have, at its cephalad end, a generally semicircular perimeter 344. In some embodiments, fixation pegs may be used to anchor the tibial prosthesis 104 to the adjoining bone, as described above in connection with the talar prosthesis 102.

A wide variety of instruments and methods may be used to prepare the receiving surfaces of the talus and the tibia to receive the talar prosthesis 102 and the tibial prosthesis 104, respectively. One exemplary instrument set will be shown and described in connection with FIGS. 4 through 15, along with one exemplary method. Those of skill in the art will recognize that each of the implants, instruments, and methods set forth herein may be used independently of the others, and/or with alternative implants, instruments, or methods.

In some embodiments, it may be beneficial to prepare the talus and/or the tibia from along an anterior approach (i.e., an approach by which instruments are inserted into the joint space from anterior to the joint space). The anterior approach may be less invasive and may minimize trauma, thereby expediting recovery times. In some known procedures, a lateral approach was used to form anterior-posterior curvatures on the prepared surfaces of the talus and/or the tibia to preserve more of the bone that is to underlie the implants. However, known instruments are generally unable to generate anterior-posterior curves from other approaches, such as an anterior approach.

According to some embodiments, the surgeon may initiate the arthroplasty procedure may accessing an anterior aspect of the ankle joint. This may be done, for example, by cutting and retracting tissues that lie anterior to the joint space (i.e., on the anterior surface of the ankle). The joint space may then be exposed. The surgeon may then attach one or more guide assemblies to the talus and/or the tibia to guide motion of one or more cutting tools.

In some examples, a talar guide assembly may first be secured to the talus and used to guide motion of a cutting tool to prepare the talus to receive the talar prosthesis 102. This will be shown and described in connection with FIGS. 4A through 12. Part of the talar guide assembly may then be used to properly locate a tibial guide assembly, which may be registered on the talar guide assembly and then secured to the tibia. This will be shown and described in connection with FIGS. 13A through 13C. The tibial guide assembly may be used to guide motion of a cutting tool to prepare the tibia to receive the tibial prosthesis 104. This will be shown and described in connection with FIGS. 14A through 15. Then, the talar prosthesis 102 and the tibial prosthesis 104 may be inserted and secured to the talus and the tibia, respectively. The resulting joint space, after completion of the ankle arthroplasty procedure, will be shown and described in connection with FIG. 16.

FIGS. 4A through 4C are cephalad perspective, caudal perspective, and cephalad perspective views, respectively, of a trial 400 that may be used to position a talar foundation 410 relative to a talus 420 through the use of a column 430, with the talar foundation 410 and the column 430 assembled with the talus 420 and the trial 400 in FIG. 4C. The talus 420 may have a natural articular surface 422 that is to be replaced via an arthroplasty procedure.

As shown, the trial 400 may have a cephalad side 440 and a caudal side 442. The cephalad side 440 may have a column mounting feature 444 that interfaces with a corresponding feature (not shown) on the column 430. As shown, the column mounting feature 444 may have an ovoid shape with apertures that may interface with a corresponding ovoid recess and/or bosses on the column 430. The caudal side 442 may have a talar foundation registration feature 446 that mates with the talar foundation 410 to temporarily couple the trial 400 to the talar foundation 410 so that rotation of the trial 400 causes the talar foundation 410 to rotate as well. The talar foundation registration feature 446 may have a hole 448 and a rectangular boss 450 surrounding the hole 448.

Further, the trial 400 may have an anterior end 460 and a posterior end 462. When the trial 400 rests on the talus 420, the anterior end 460 may extend over the anterior portion of the talus 420 and the metacarpals, and the posterior end 462 may rest on the natural articular surface 422 of the talus 420. The anterior end 460 may have an anterior window 464 that can be used to visually align the anterior end 460 with the talus 420 and/or metacarpals. The posterior end 462 may have a posterior window 456 that facilitates visualization of the natural articular surface 422 and/or alignment of the posterior end 462 with the natural articular surface 422. The posterior end 462 may also have a concave curvature 458 dimensioned to allow the posterior end 462 to fit relatively snugly on the natural articular surface 422.

The column 430 may have a proximal end (not shown) and a distal end 470. The distal end 470 may have a trial receiver 472, in which there is a trial mounting feature (not shown) securable to the column mounting feature 444 of the trial 400. The trial receiver 472 may also have a hole 474 that aligns with the hole 448 of the talar foundation registration feature 446 when the column 430 is attached to the trial 400, thereby providing access to the hole 448. The proximal end of the column 430 may have an alignment feature such as a pin, hole, or marking, that can be easily aligned with a landmark on the patient's leg, proximal to the talus. In some embodiments, this landmark may be a tibial tubercle on a proximal end of the tibia. Thus, the column 430 may have a length sufficient to span substantially the entire length of the patient's tibia.

When the proximal end of the column 430 is rotated to the desired alignment with the tibial tubercle, the distal end may also rotate, causing the trial 400 to rotate on the talus 420. This rotation may also cause the talar foundation 410 to rotate to the desired orientation relative to the talus 420. The talar foundation 410 may then be fixed relative to the talus 420, for example, through the use of pins 480 that are inserted through the talar foundation 410 and are driven into the talus 420. The pins 480 may be oriented obliquely relative to each other so that the talar foundation 410 is unable to slide toward or away from the talus 420 along the pins 480. After the talar foundation 410 has been fixed in place relative to the talus 420, the trial 400 and the column 430 may be removed from the talar foundation 410.

FIGS. 5A, 5B, and 5C are posterior cephalad perspective, anterior cephalad perspective, and anterior cephalad perspective views, respectively, of the talar foundation 410 of FIG. 4C, with the talar foundation 410 fixed to the talus 420 in FIG. 5C. The talar foundation 410 may be designed as a stable attachment point to position and/or move other instruments relative to the talus 420 and/or the tibia. The talar foundation 410 may have a stationary member 500 and a mobile member 502, which may be movably coupled to the stationary member 500.

The stationary member 500 may have a bone attachment interface that facilitates attachment of the stationary member 500 to the talus 420. Any bone attachment feature known in the art may be used; in the embodiment of FIGS. 5A through 5C, the bone attachment interface may take the form of a series of passageways 510 through which the pins 480 are inserted. The passageways 510 may be oriented obliquely relative to each other so that the pins 480 are nonparallel to each other. Thus, when the pins 480 are in place, the position and orientation of the talar foundation 410 may substantially fixed relative to the talus 420. There may be more of the passageways 510 than are needed for fixation of the talar foundation 410; accordingly, the surgeon may only insert the pins 480 through the passageways 510 that are positioned for optimal anchorage of the pins 480 in the talus 420.

The stationary member 500 may also have a mobile member interface that provides movable coupling of the mobile member 502 to the stationary member 500. As embodied in FIGS. 5A through 5C, the mobile member 502 rotates relative to the stationary member 500. In alternative embodiments (not shown), instead of pure rotation, a foundation may have a mobile member that translates and/or undergoes some combination of translation and rotation relative to a stationary member. Any movable coupling known in the art may be used, including but not limited to pin joints, sliding joints, linkages, and the like.

In FIGS. 5A through 5C, the mobile member interface may take the form of a pair of arcuate slots 512 that extend anterior-posteriorly and cephalad-caudally. The arcuate slots 512 may be centered on an axis 514 extending medial-laterally. As shown in FIG. 5C, the axis 514 may be positioned caudal and posterior to the arcuate slots 512. From the outward-facing sides of the stationary member 500, the arcuate slots 512 may be recessed within arcuate grooves 516 that follow the same arcuate pathway as the arcuate slots 512. Two or more sets of detents 518 may be formed on each side of the stationary member 500. The detents 518 may extend generally medial-laterally, and may help control the range of motion of the mobile member 502 relative to the stationary member 500, as will be discussed subsequently.

Further, the stationary member 500 may have a trial interface that couples the stationary member 500 to the trial 400. It may be desirable for the trial interface to provide fixed attachment between the stationary member 500 and the trial 400 so that the position and orientation of the trial 400 determine the position and orientation of the stationary member 500, and thence of the talar foundation 410.

As embodied in FIGS. 5A through 5C, the trial interface may be a hole 520 that resides in a rectangular recess 522. A fastener, such as a screw or bolt, may be inserted through the talar foundation registration feature 446 of the trial 400. The fastener may be inserted through the hole 474 of the trial receiver 472 and through the hole 448 of the talar foundation registration feature 446, and may anchor in the hole 520. The rectangular recess 522 may receive the rectangular boss 450 of the talar foundation registration feature 446 to ensure that, with the column 430 and the trial 400 attached to the stationary member 500, the stationary member 500 is unable to rotate relative to the trial 400 or the column 430.

The mobile member 502 may have a stationary member interface that cooperates with the mobile member interface of the stationary member 500 to provide movable coupling between the stationary member 500 and the mobile member 502. The stationary member interface may be selected to provide rotatable coupling between the stationary member 500 and the mobile member 502.

In FIGS. 5A through 5C, the stationary member interface may include rollers 530 that reside in the arcuate grooves 516, and are rotatably anchored to the main body of the mobile member 502 through the arcuate slots 512. There may be two of the rollers 530 in each of the arcuate grooves 516 to ensure that the mobile member 502 is unable to rotate freely, relative to the stationary member 500, but is instead constrained to rotate predictably relative to the stationary member 500 as the rollers move along the arcuate grooves 516. Thus, the mobile member 502 may be constrained to rotate relative to the stationary member 500 about the axis 514.

In addition to the rollers 530, the mobile member 502 may have a guide knob 540 that protrudes from the medial side or the lateral side of the mobile member 502. In some embodiments, the guide knob 540 may be rotatable relative to the remainder of the mobile member 502 such that the guide knob 540 can be tightened to frictionally engage the stationary member 500, thereby preventing relative rotation between the stationary member 500 and the mobile member 502, or loosened to permit the mobile member 502 to rotate relative to the stationary member 500. Thus, the surgeon may engage the guide knob 540 to temporarily fix the mobile member 502 in place relative to the stationary member 500 to make cuts with the mobile member 502 in its current position and orientation, prior to disengaging the guide knob 540 to move the mobile member 502 to a new position and orientation.

The mobile member 502 may also have abutments (not shown) facing toward the stationary member 500 such that the abutments engage the detents 518 when the mobile member 502 is at two or more predetermined positions relative to the stationary member 500. The predetermined positions may be, for example, the desired anterior and posterior motion limits of the mobile member 502 relative to the stationary member 500. For example, when the mobile member 502 is positioned such that the abutments engage the detents 518 on the anterior of the stationary member 500, the engagement of the abutments with the detents 518 may prevent the mobile member 502 from moving further anteriorly, relative to the stationary member 500. This may be the position depicted in FIGS. 5A through 5C. Similarly, when the mobile member 502 is positioned such that the abutments engage the detents 518 on the posterior of the stationary member 500, the engagement of the abutments with the detents 518 may prevent the mobile member 502 from moving further posteriorly, relative to the stationary member 500.

In the alternative, the engagement of the abutments with the detents 518 may not establish motion limits, but may rather provide tactile response, indicating to the surgeon that the mobile member 502 has reached an anterior or posterior reference position relative to the stationary member 500. Specifically, engagement of the abutments with the detents 518 may be heard and/or felt by the surgeon as the abutments snap or click into the detents 518. Thus, the surgeon may be aware that further anterior or posterior motion of the mobile member 502 relative to the stationary member 500 may cause the mobile member 502 to pass beyond a predetermined reference point.

The mobile member 502 may also have a tool holder attachment interface, or more specifically, a talar burr holder interface attachable to a talar burr holder that holds a cutting tool in the form of a burr. The talar burr holder may have a base that is attachable to the talar burr holder interface; thus, the talar burr holder interface may also be called a base attachment interface. The base attachment interface may be designed to secure the base relative to the mobile member 502 such that the mobile member 502 carries the base as it moves relative to the stationary member 500. As will be described subsequently, the base attachment interface may also be used to attach an alignment block to the mobile member 502 to facilitate positioning of a tibial foundation relative to a tibia.

In FIGS. 5A through 5C, the base attachment interface may take the form of a pair of threaded holes 550 in the mobile member 502. The threaded holes 550 may receive fasteners, such as screws or bolts, which can be used to hold the base in place on the mobile member 502. The configuration and operation of the talar burr holder will be shown and described in connection with FIGS. 6A through 11B.

Figure 6A:
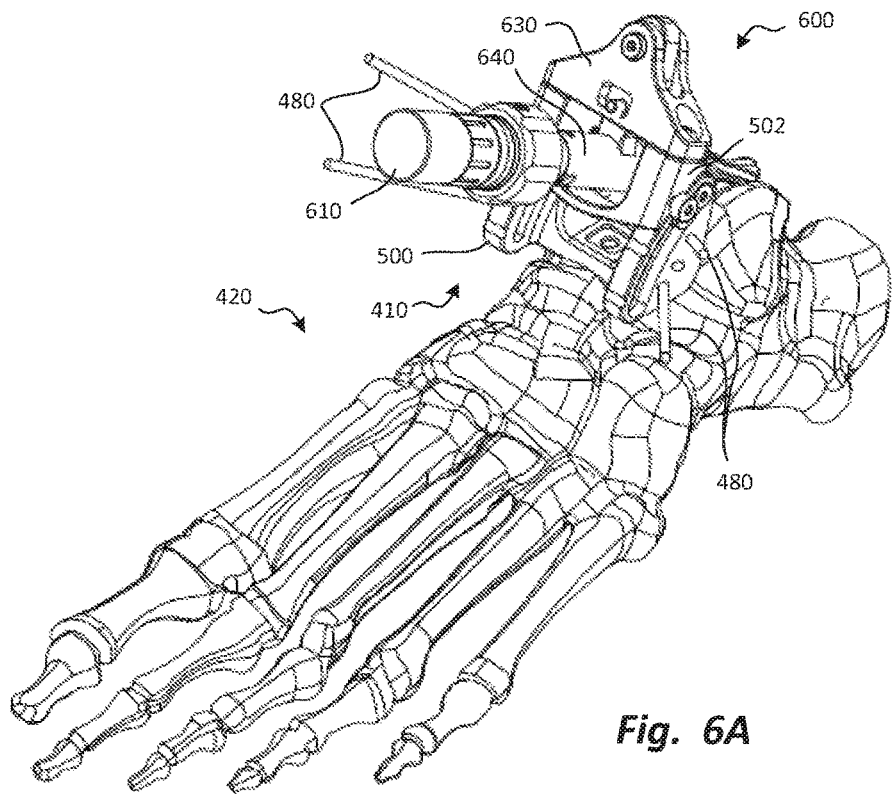
FIGS. 6A and 6B are anterior perspective and posterior perspective views, respectively, of a talar burr holder secured to the talar foundation to hold a burr relative to the talus.
Figure 6B:
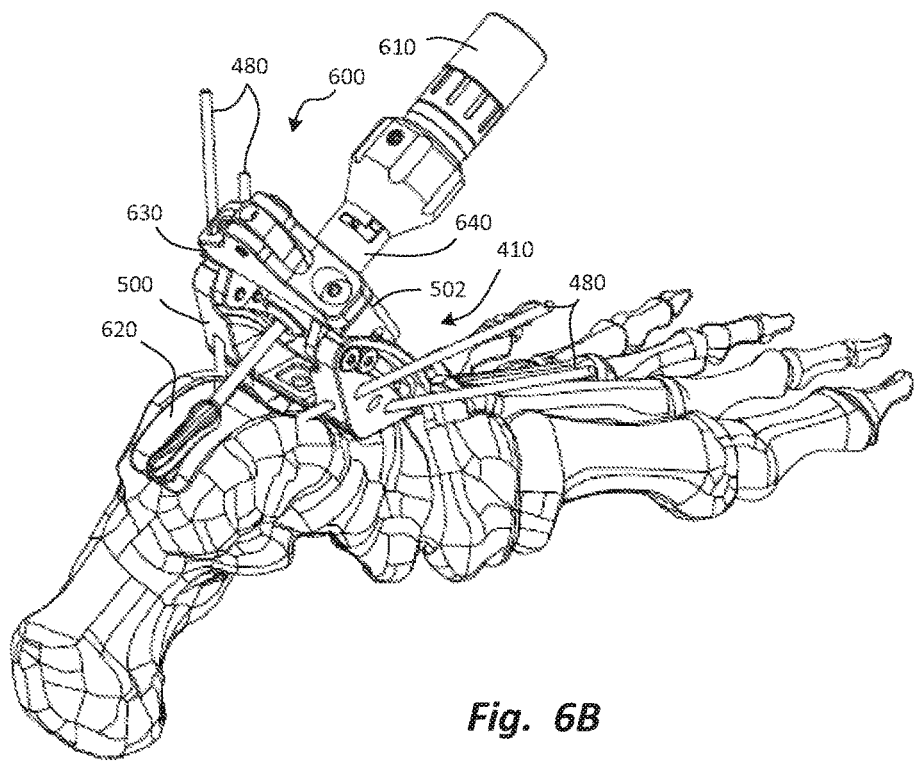

FIGS. 6A and 6B are anterior perspective and posterior perspective views, respectively, of a talar burr holder 600 secured to the talar foundation 410 to hold a burr 610 relative to the talus 420. The talar foundation 410 and the talar burr holder 600, combined, may define a talar guide assembly that guides motion of the burr 610 relative to the talus 420 to form a prepared surface 620 on the talus 420 that is shaped to receive a prosthesis, such as the talar prosthesis 102 of FIGS. 1A through 2E.

Specifically, the talar burr holder 600 may be secured to the mobile member 502 of the talar foundation 410 so that the talar burr holder 600 is pivotable relative to the stationary member 500 and the talus 420 along with the mobile member 502. The talar burr holder 600 may also enable further motion (for example, medial-laterally and cephalad-caudally) of the burr 610 to generate the desired contour of the prepared surface 620. Use of the burr 610 is merely exemplary; those of skill in the art will recognize that a wide variety of cutting tools may be used to form the prepared surface 620. Such cutting tools may include rotating and/or translating tools such as burrs, reamers, reciprocating saws, and/or the like.

As shown, the talar burr holder 600 may have a base 630 that is fixedly secured to the mobile member 502 of the talar foundation 410, and an arm 640 that moves relative to the base 630. Motion of the arm 640 relative to the base 630 may enable the burr 610 to move medial-laterally on the talus 420, in addition to the anterior-posterior rotation provided by the motion of the mobile member 502 relative to the talus 420. The burr 610, along with additional burrs that may be used in connection with the arthroplasty process, will be described in greater detail in connection with FIGS. 7A through 8C.

Figure 7A:
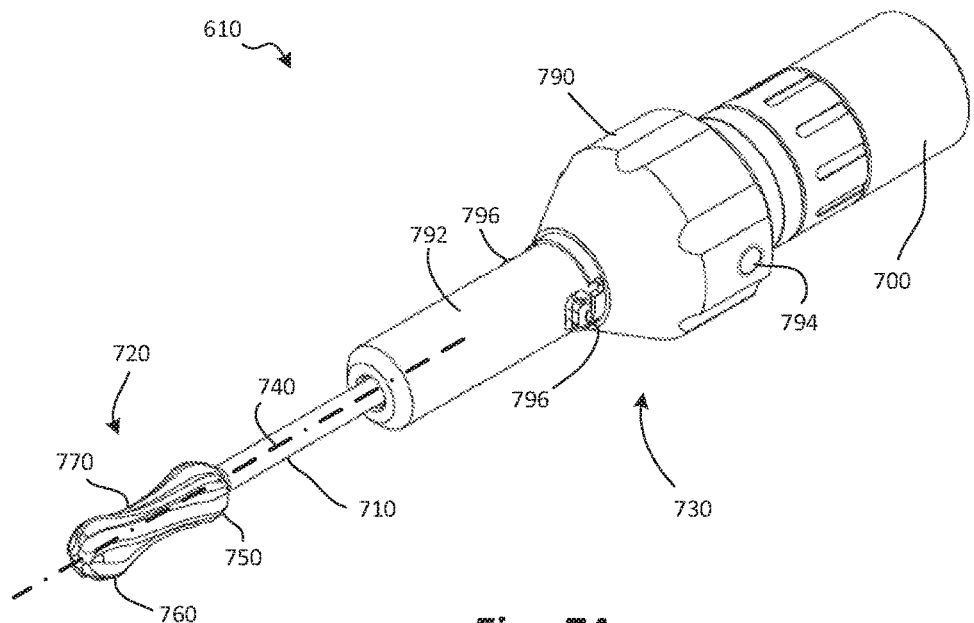
FIGS. 7A through 7C are perspective, side elevation, and plan, section views, respectively, of the burr of FIGS. 6A and 6B.
Figure 7B:
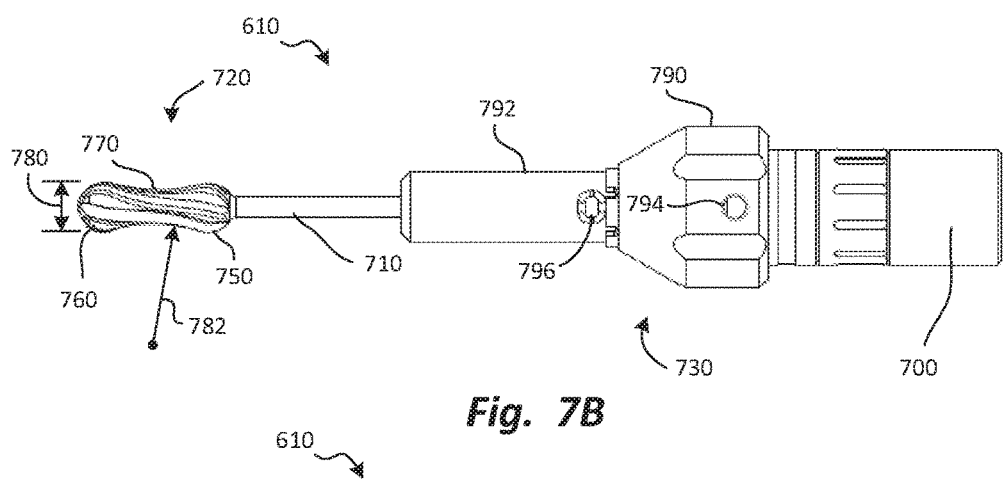
Figure 7C:
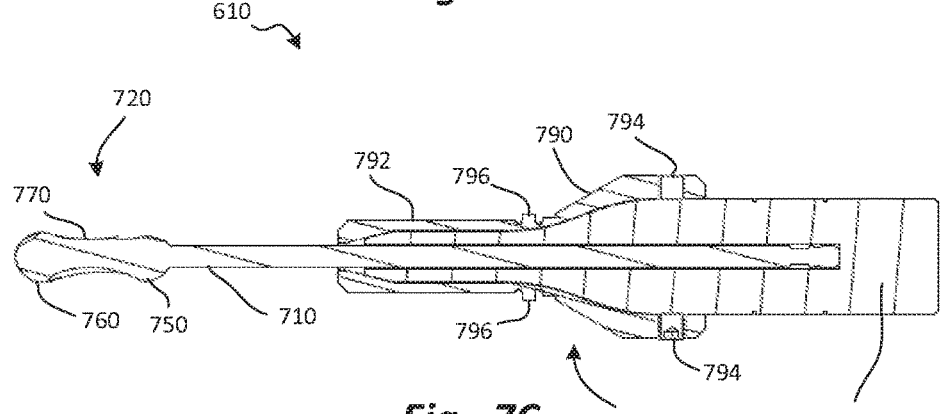

FIGS. 7A through 7C are perspective, side elevation, and plan, section views, respectively, of the burr 610. The burr 610 may have a body 700, a shaft 710, and a cutting element 720. An adapter 730 may be used to couple the burr 610 to the talar burr holder 600. The body 700 may be generally cylindrical in shape, and may contain a rotary motor (not shown). The rotary motor may induce the shaft 710 to rotate relative to the body 700; the shaft 710 may also be cylindrical in shape. The cutting element 720 may be carried by the shaft 710; thus, rotation of the shaft 710 may drive rotation of the cutting element 720.

The cutting element 720 and the shaft 710 may rotate about a cutting tool axis 740 parallel to the length of the cutting element 720. The cutting element 720 may have a concave shape that facilitates formation of a convex anterior-posterior curvature from an anterior approach. Specifically, the cutting element 720 may have a proximal end 750, a distal end 760, and an intermediate portion 770 between the proximal end 750 and the distal end 760. The proximal end 750 and the distal end 760 may both be enlarged relative to the intermediate portion 770, and may share a maximum radius 780, perpendicular to the cutting tool axis 740. The radius of the intermediate portion 770 may be much smaller. The maximum radius 780 may be substantially the same as the radius of medial-lateral curvatures present in the prepared surface 620 to be formed on the talus 420 by the cutting element 720.

In-plane with the cutting tool axis 740, the cutting element 720 may have an arcuate concave profile with a radius 782 defined by the change in diameter of the cutting element 720, from the proximal end 750 to the intermediate portion 770, and then to the distal end 760. The radius 782 may be substantially the same as the radius of an anterior-posterior curvature present in the prepared surface 620 to be formed on the talus 420 by the cutting element 720.

The adapter 730 may have a flared proximal end 790, a cylindrical distal end 792, a pair of body attachment holes 794, and a pair of burr holder attachment bosses 796. The proximal end 790 may be hollow, and may be sized to accommodate the body 700 of the burr 610. The cylindrical distal end 792 may similarly be sized to accommodate the shaft 710 of the burr 610, and/or surrounding material. The body attachment holes 794 may facilitate secure attachment of the adapter 730 to the burr 610. According to some examples, fasteners such as set screws may be inserted into the body attachment holes 794 to anchor the adapter 730 to the burr 610. The burr holder attachment bosses 796 may be used to facilitate attachment of the adapter 730, and thence the burr 610, to the talar burr holder 600 and/or a tibial burr holder, which will be shown and described subsequently.

According to some examples, the body 700 may be that of a standard orthopedic burr or reamer. The cutting element 720 and the adapter 730 may be used to customize such a standard orthopedic burr or reamer for formation of the prepared surface 620 from an anterior approach.

A variety of different cutting elements may be used in addition to or in the alternative to the cutting element 720. Such cutting elements may have convex or straight shapes. Examples will be shown and described in connection with FIGS. 8A through 8C.

Figure 8A:
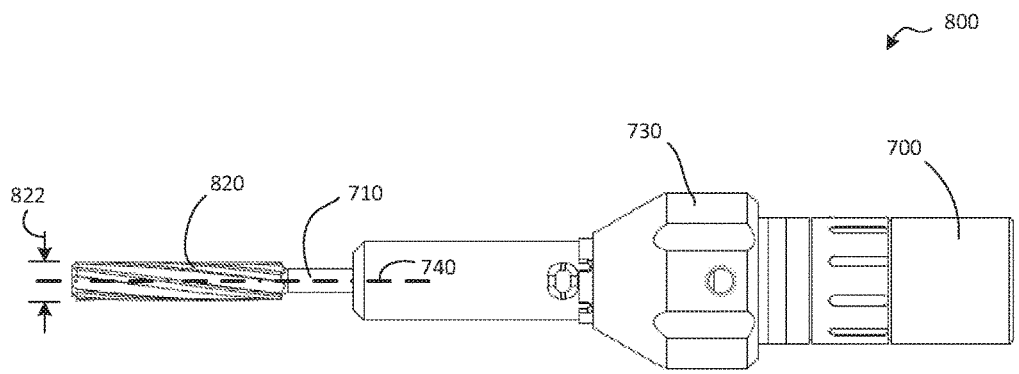
FIGS. 8A through 8C are side elevation views of burrs according to various embodiments.
Figure 8B:
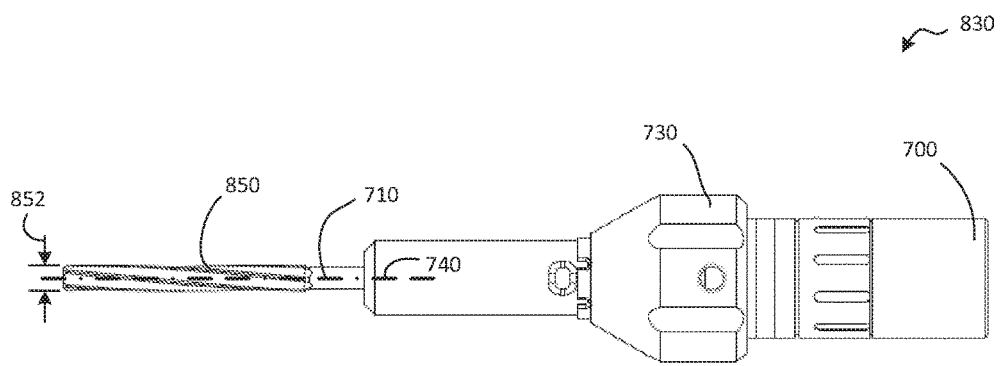
Figure 8C:
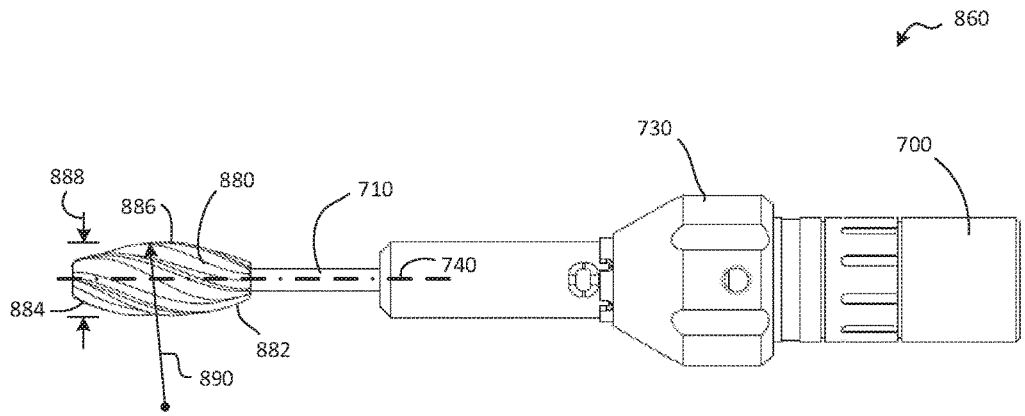

FIGS. 8A through 8C are side elevation views of a burr 800, a burr 830, and a burr 860, respectively, according to various embodiments. The burr 800, the burr 830, and the burr 860 may each be used in conjunction with an adapter 730 like that of FIGS. 7A through 7C, and may have components similar to those of the burr 610, including a body 700 and a shaft 710. Each of the burr 800, the burr 830, and the burr 860 may be configured for rotation about a cutting tool axis 740 like that of the burr 610. However, the cutting elements of the burr 800, the burr 830, and the burr 860 may be configured differently.

Specifically, the burr 800 may have a cutting element 820 with a straight, generally cylindrical shape. The cutting element 820 may have a diameter 822 suitable for cutting a space in the prepared surface 620 for the keel 212 of the talar prosthesis 102. The diameter of the cutting element 820 may likewise be suitable for cutting a space for the keel 312 of the tibial prosthesis 104.

The burr 830 may also have a cutting element 850 with a straight, generally cylindrical shape. The cutting element 850 may have a diameter 852 suitable for cutting a space in the prepared surface 620 for the shaft 710, for example, of the burr 610, the burr 800, and/or the burr 860. Thus, the burr 830 may be used as a lead-in to provide space in which the shaft 710 can move in future bone removal steps.

The burr 860 may be used to form a concave anterior-posterior curvature in the tibia. Thus, the burr 860 may have a cutting element 880 with a generally convex shape. Specifically, the cutting element 880 may have a proximal end 882, a distal end 884, and an intermediate portion 886 between the proximal end 882 and the distal end 884. The intermediate portion 886 may be enlarged relative to the proximal end 882 and the distal end 884, and may have a maximum radius 888, perpendicular to the cutting tool axis 740. The radii of the proximal end 882 and the distal end 884 may be much smaller. The maximum radius 888 may be substantially the same as the radius of medial-lateral curvatures present in a prepared surface to be formed on the tibia by the cutting element 880.

In-plane with the cutting tool axis 740, the cutting element 880 may have an arcuate convex profile with a radius 890 defined by the change in diameter of the cutting element 880, from the proximal end 882 to the intermediate portion 886, and then to the distal end 884. The radius 890 may be substantially the same as the radius of an anterior-posterior curvature present in the prepared surface to be formed on the tibia by the cutting element 880.

FIGS. 9A through 9C are cephalad perspective caudal perspective, and anterior elevation, section views, respectively, of the talar burr holder 600 of FIGS. 6A and 6B. The talar burr holder 600 may be designed to hold one or more cutting tools in order to facilitate formation of the prepared surface 620 in the talus 420.

Specifically, the talar burr holder 600 may be used to hold the burr 830 to remove an anterior portion of the natural articular surface 422, thereby providing space for the shaft 710 of the burr 610 and the shaft 710 of the burr 800. Then, talar burr holder 600 may be used to hold the burr 610 to remove the remainder of the natural articular surface 422 of the talus 420, thereby forming a convex anterior-posterior curvature of the prepared surface 620. The talar burr holder 600 may also be used to form a slot generally in the shape of the keel 212 of the talar prosthesis 102. Thus, after usage of the talar burr holder 600 in combination with the burr 830, the burr 610, and the burr 800, the prepared surface 620 may be shaped to receive the talar bone engagement surface 112 of the talar prosthesis 102. These steps may be re-ordered, and will be described in greater detail subsequently.

The base 630 of the talar burr holder 600 may have a foundation interface that can be used to attach the base 630 to the talar foundation 410. The foundation interface may have any structure suitable for securing the base 630 to the talar foundation 410. As embodied in FIGS. 9A through 9C, the foundation interface may include two holes 900 that are spaced apart in a manner similar to that of the threaded holes 550 of the mobile member 502 of the talar foundation 410. The holes 900 may be smooth-bored. Accordingly, fasteners 902, which may be screws, bolts, or the like, may be inserted through the holes 900 and rotated into engagement with the threaded holes 550 of the mobile member 502 of the talar foundation 410 to secure the base 630 to the mobile member 502.

The base 630 may further have an arm coupling feature by which the arm 640 is coupled to the base 630. The base 630 and the arm 640 may be movably coupled together through any combination of rotating and/or sliding joints. According to some embodiments, the arm coupling feature provides a rotatable coupling between the base 630 and the arm 640.

As shown in FIGS. 9A through 9C, the arm coupling feature may include a pin 910 about which the arm 640 is rotatably mounted. The pin 910 may have a head 912 and a shank 914 with male threads that can engage corresponding female threads in a hole 916 in the base 630. The head 912 may have an interface that permits rotation of the head 912 with a tool such as a screwdriver to facilitate assembly of the talar burr holder 600. The head 912 may reside within a hole 918 in the base 630. A portion of the shank 914 adjacent to the head 912 may be smooth so that the arm 640 can engage and rotate smoothly on it. The base 630 may further have two parallel plates, an anterior plate 920 and a posterior plate 922, between which the proximal portion of the arm 640 is captured. The hole 918 in which the head 912 resides may be formed in the anterior plate 920, and the hole 916 in which the shank 914 is anchored may be formed in the posterior plate 922. Thus, the pin 910 may be inserted posteriorly, through the hole 918 in the anterior plate 920 to anchor in the hole 916 in the posterior plate 922.

Further, the base 630 may have a base guide feature that helps to guide motion of the arm 640 relative to the base 630. The base guide feature may cooperate with a corresponding arm guide feature of the arm 640 to limit the range of motion of the arm 640, thereby limiting the range of motion of the attached cutting tool, such as the burr 610, the burr 800, or the burr 830, relative to the talus 420. As embodied in FIGS. 9A through 9C, the base guide feature may include a rectangular window 930 with four guide surfaces 932. The guide surface 932 that is positioned caudally (and oriented to face in the cephalad direction) may serve to limit motion of the cutting tool in the caudal direction toward the talus 420, as will be described subsequently.

As shown in FIG. 9C, the arm 640 may be divided into a first arm member 950 and a second arm member 952. The second arm member 952 may be nested within the first arm member 950 such that the second arm member 952 is slidable within the first arm member 950 so that the arm 640 effectively has adjustable reach relative to the pin 910. A resilient member may be used to bias the first arm member 950 apart from the second arm member 952, thereby urging the arm 640 toward its maximum length. The resilient member may take the form of a linear spring 954 that is normally held under compression. The linear spring 954 may reside partially in a cavity in the distal end of the second arm member 952.

The arm 640 may have a base coupling feature by which the arm 640 is coupled to the base 630. The base coupling feature may be configured in a variety of ways, and may be designed to cooperate with the arm coupling feature of the base 630. In FIGS. 9A through 9C, the base coupling feature may include a slot 960 formed in the proximal end of the first arm member 950, and a cradle 962 formed in the proximal end of the second arm member 952. The slot 960 may be elongated cephalad-caudally, and may receive the pin 910 to allow the first arm member 950 to move upward or downward relative to the pin 910. The cradle 962 may be concave and semicircular in shape so that the proximal end of the second arm member 952 abuts and slides relatively smoothly relative to the pin 910, while permitting the proximal end of the second arm member 952 to push upward against the pin 910, urging the first arm member 950 downward.

The arm 640 may further have a tool attachment interface to which a cutting tool can be attached. Where the cutting tool is a burr such as the burr 610, the burr 800, the burr 830, and/or the burr 860, the tool attachment interface may be referred to as a burr attachment interface. The burr attachment interface may be designed to hold any of the burr 610, the burr 800, and the burr 830 in a fixed relationship to the first arm member 950. More precisely, the burr attachment interface may be designed to receive and secure the adapter 730 secured to one of the burr 610, the burr 800, and the burr 830.

As depicted in FIGS. 9A through 9C, the burr attachment interface may take the form of an attachment cannula 970 with a bore 972 sized to receive the cylindrical distal end 792 of the adapter 730. The attachment cannula 970 may also have one or more locking features that can selectively lock the adapter 730 in place relative to the attachment cannula 970. The locking features may operate as bayonet fittings; thus, they may take the form of slots 974 that extend axially, and then circumferentially, on the attachment cannula. Each of the slots 974 may be sized to receive one of the burr holder attachment bosses 796 of the adapter 730.

Specifically, the adapter 730 may be attached to the corresponding cutting tool, and then inserted posteriorly into the attachment cannula 970 such that the burr holder attachment bosses 796 enter the axially-extending portions of the slots 974. Once the burr holder attachment bosses 796 have reached the ends of the axially-extending portions, the adapter 730 may be rotated about the axis of the attachment cannula 970, which may be collinear with the cutting tool axis 740 of the cutting tool, so that the burr holder attachment bosses 796 slide along the circumferentially-extending portions of the slots 974. One or more snap features (not shown) may optionally cause the adapter 730 to snap in place in the attachment cannula 970. In any case, the combination of axial translation and rotation needed to attach the adapter 730 to the attachment cannula 970 may ensure that the cutting tool is securely held relative to the first arm member 950, until the insertion motion is made in reverse.

Yet further, the arm 640 may have an arm guide feature that cooperates with the base guide feature to constrain motion of the arm 640 relative to the base 630. The arm guide feature may be any member that can interact with the base guide feature to help constrain relative motion between the base 630 and the arm 640. Where the base guide feature includes guide surfaces, the arm guide feature may advantageously be a follower that can abut and/or rest against such guide surfaces.

Specifically, the base guide feature may be a post 980 protruding from the first arm member 950, between the pin 910 and the attachment cannula 970. The post 980 may protrude anteriorly such that the post 980 resides in the rectangular window 930 of the base 630. The interaction of the post 980 with the guide surfaces 932 of the rectangular window 930 may limit motion of the attachment cannula 970, and thence the cutting tool, to a generally rectangular zone. In particular, the guide surface 932 on the bottom of the rectangular window 930 may limit motion of the cutting tool toward the talus 420, thereby controlling the depth of the resection.

More particularly, the guide surface 932 on the bottom of the rectangular window 930 may prevent the cutting tool axis 740 of the burr 610, the burr 800, or the burr 830 from moving closer to the talus 420 than a planar boundary. Similarly, the guide surfaces 932 on the sides of the rectangular window 930 may prevent the cutting tool axis 740 of the burr 610, the burr 800, or the burr 830 from moving further medially or laterally than additional planar boundaries. Thus, the post 980 of the arm 640 may cooperate with the rectangular window 930 of the base 630 to ensure that the prepared surface 620 has the desired depth, width, and overall shape.

The action of the linear spring 954 may also help ensure that the prepared surface 620 has the desired shape. Specifically, the pressure exerted by the linear spring 954 may help ensure that cuts made to the talus 420 extend to the full desired depth, thereby ensuring that the prepared surface 620 has the depth and consistency needed to provide a continuous expanse of bone to support the talar prosthesis 102. Nevertheless, the linear spring 954 may be tuned to provide force that can easily be resisted by the surgeon in order to remove bone with shallower cuts prior to extending the cutting tool to the full depth permitted by the interaction of the post 980 with the rectangular window 930. The manner in which the talar cutting guide, including the talar foundation 410 and the talar burr holder 600, may be used to control the resection of the talus 420 will be shown and described in greater detail in connection with FIGS. 6A, 6B, and 10A through 12.

Returning briefly to FIGS. 6A and 6B, the talar foundation 410 and the talar burr holder 600 may, in some embodiments, be used to form the prepared surface 620 commencing with the posterior aspect of the prepared surface 620. Specifically, with the base 630 secured to the mobile member 502 of the talar foundation 410 and the burr 830 secured to the arm 640, the mobile member 502 may be pivoted, relative to the stationary member 500, toward its posterior position. This may position the cutting element 850 of the burr 830 over the posterior portion of the natural articular surface 422 of the talus 420. The surgeon may hold the burr 830 above the natural articular surface 422, against the force of the linear spring 954, with the post 980 displaced from the guide surface 932 at the bottom of the rectangular window 930, until he or she is ready to begin resecting the natural articular surface 422.

The surgeon may then lower the burr 830, allowing the linear spring 954 to press the burr 830 to engage the natural articular surface 422, until the post 980 rests against the guide surface 932 at the bottom of the rectangular window 930. The burr 830 may then be moved medial-laterally (i.e., from side-to-side) by moving the attachment cannula 970 medial-laterally, causing the post 980 to slide medial-laterally along the guide surface 932 at the bottom of the rectangular window 930. The post 980 may abut the guide surfaces 932 at the left and right sides of the rectangular window 930 to control the extent of medial-lateral motion of the burr 830.

Once the burr 830 has passed over the medial-lateral extents of the natural articular surface 422, the mobile member 502 may be rotated anteriorly relative to the stationary member 500 to move the burr 830 toward the anterior portion of the natural articular surface 422. Medial-lateral motion of the burr 830 may be repeated to remove material from the anterior portion of the natural articular surface 422 as needed. If desired, medial-lateral motion of the burr 830 may also be carried out during anterior rotation of the mobile member 502 to remove material from the full anterior-posterior curvature of the natural articular surface 422.

As mentioned previously, the purpose of the burr 830 may simply be to remove sufficient material to permit the burr 610 and the burr 800 to engage the talus 420 without impediment, particularly by removing bone from where the shaft 710 of the burr 610 and the shaft 710 of the burr 800 will be positioned in future cutting steps. Thus, the burr 830 need not be used to resect away the entirety of the natural articular surface 422.

Once the burr 830 has been passed over the medial-lateral and anterior-posterior extents of the natural articular surface 422, the burr 830 may be removed from the attachment cannula 970, and the burr 610 may instead be secured to the attachment cannula 970. The burr 610 may then be positioned over the posterior portion of the natural articular surface 422. The surgeon may hold the burr 610 above the natural articular surface 422, which has now been partially resected, against the force of the linear spring 954. Again, the post 980 may be displaced from the guide surface 932 at the bottom of the rectangular window 930 until the surgeon is ready to begin resecting the natural articular surface 422 with the burr 610.

The surgeon may then lower the burr 610, allowing the linear spring 954 to press the burr 610 to engage the natural articular surface 422, until the post 980 rests against the guide surface 932 at the bottom of the rectangular window 930. This is the position depicted in FIGS. 6A and 6B. The burr 610 may then be moved medial-laterally (i.e., from side-to-side) by moving the attachment cannula 970 medial-laterally, causing the post 980 to once again slide medial-laterally along the guide surface 932 at the bottom of the rectangular window 930. The post 980 may abut the guide surfaces 932 at the left and right sides of the rectangular window 930 to control the extent of medial-lateral motion of the burr 610.

Once the burr 610 has passed over the medial-lateral extents of the natural articular surface 422, the mobile member 502 may be rotated anteriorly relative to the stationary member 500 to move the burr 610 toward the anterior portion of the natural articular surface 422. This is the position depicted in FIGS. 10A and 10B.

Figure 10A:
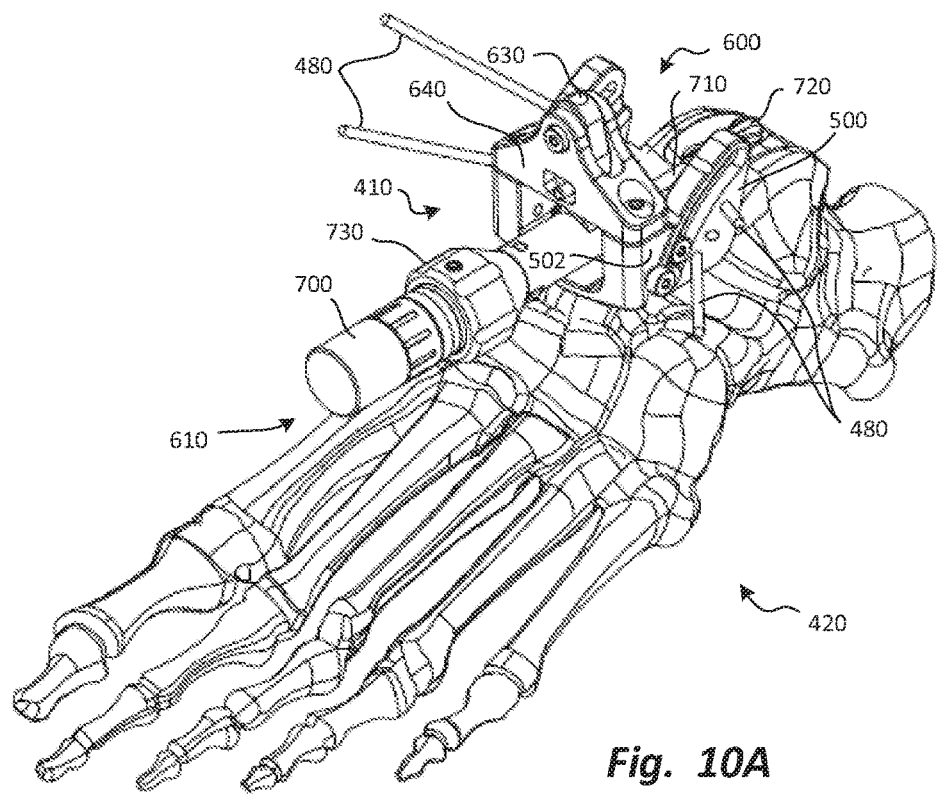
FIGS. 10A and 10B are anterior perspective and posterior perspective views, respectively, of the talus with the talar foundation attached to the talus, the talar burr holder attached to the talar foundation, and the burr positioned to resect the anterior portion of the natural articular surface of the talus.
Figure 10B:
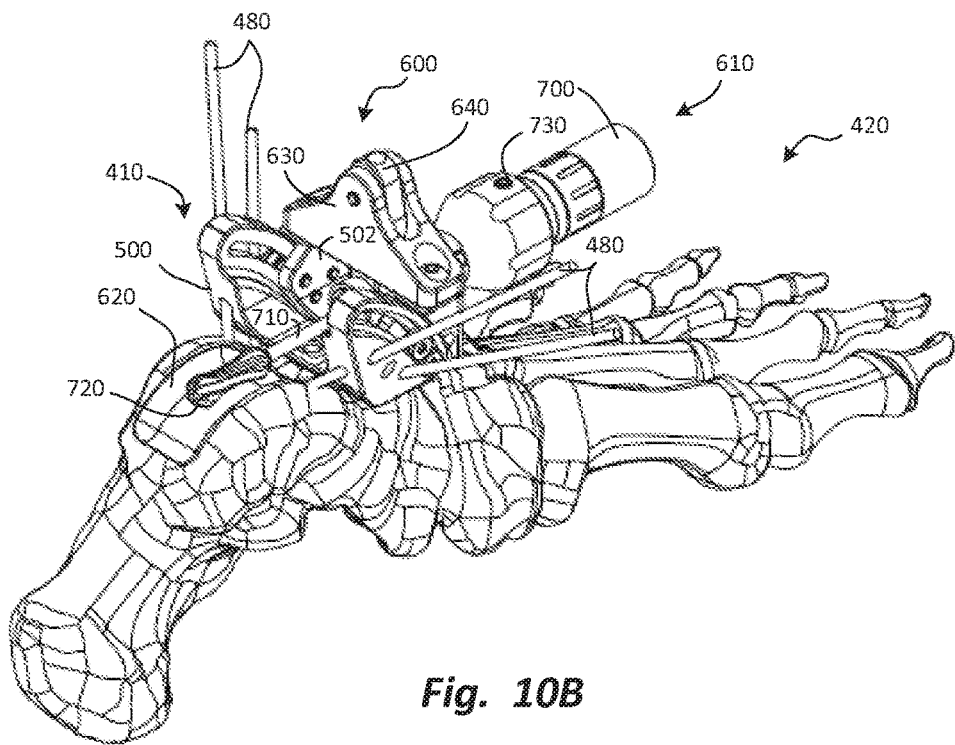

FIGS. 10A and 10B are anterior perspective and posterior perspective views, respectively, of the talus 420 with the talar foundation 410 attached to the talus 420, the talar burr holder 600 attached to the talar foundation 410, and the burr 610 positioned to resect the anterior portion of the natural articular surface 422 of the talus 420. Medial-lateral motion of the burr 610 may be repeated to remove material from the anterior portion of the natural articular surface 422 as needed. If desired, medial-lateral motion of the burr 610 may also be carried out during anterior rotation of the mobile member 502 to remove material from the full anterior-posterior curvature of the natural articular surface 422.

The result may be the formation of the prepared surface 620 as depicted in FIGS. 6B and 10B. The prepared surface 620 will be further shown and described in connection with FIGS. 11A and 11B.

Figure 11A:
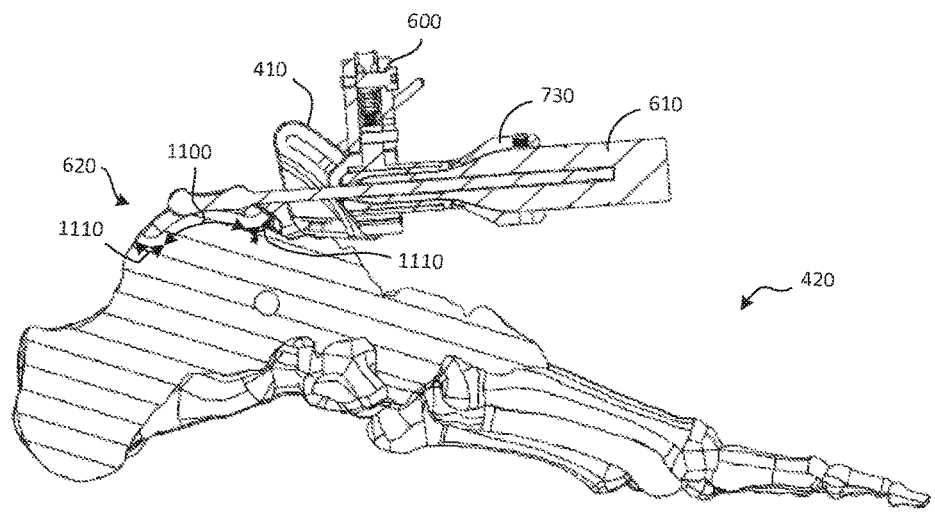
FIGS. 11A and 11B are lateral elevation, section and enlarged cephalad elevation views, respectively, of the talus with the talar foundation, the talar burr holder, and the burr positioned as in FIGS. 10A and 10B.
Figure 11B:
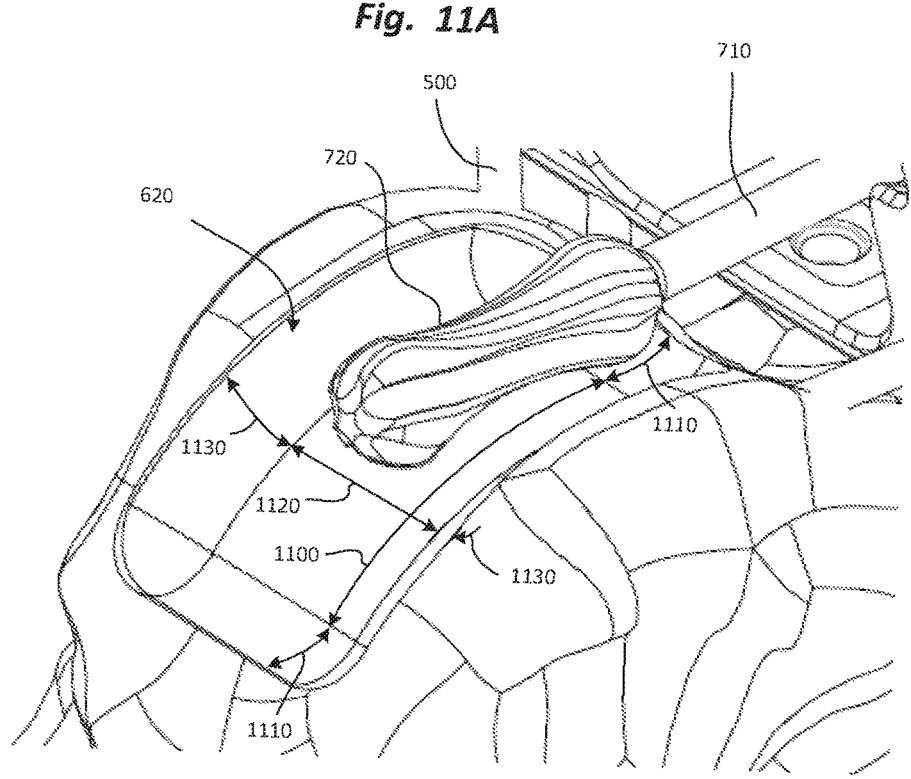

FIGS. 11A and 11B are lateral elevation, section and enlarged cephalad elevation views, respectively, of the talus 420 with the talar foundation 410, the talar burr holder 600, and the burr 610 positioned as in FIGS. 10A and 10B. The shape of the prepared surface 620, with the exception of a slot for the keel 212 of the talar prosthesis 102, is depicted in greater detail.

As shown in FIG. 11A, the prepared surface 620 may have a lateral cross-sectional shape in a plane residing in the anterior-posterior direction 130 and the cephalad-caudal direction 134 that closely matches lateral view of the talar prosthesis 102, as depicted in FIG. 2C. The prepared surface 620 may have a convex anterior-posterior curvature 1100 with a radius that is substantially the same as the anterior-posterior curvature 230 of the talar bone engagement surface 112 of the talar prosthesis 102. Anterior and posterior to the convex anterior-posterior curvature 1100, the prepared surface 620 may have two convex anterior-posterior curvatures 1110, which may have the same radius as the portions of the talar bone engagement surface 112 that lie anterior and posterior to the anterior-posterior curvature 230.

As shown in FIG. 11B, the prepared surface 620 may have a cross-sectional shape in a plane residing in the medial-lateral direction 132 and cephalad-caudal direction 134, that closely matches the cross-sectional shape of the talar bone engagement surface 112 of the talar prosthesis 102, as depicted in FIG. 2E, with the exception that a slot for the keel 212 of the talar prosthesis 102 has not yet been formed. The prepared surface 620 may have a central expanse 1120 with a generally linear shape (in cross-section), and two concave medial-lateral curvatures 1130 on either side of the central expanse 1120. The central expanse 1120 may have a width that is generally equivalent to that of the central expanse 222 of the talar bone engagement surface 112 of the talar prosthesis 102, and the concave medial-lateral curvatures 1130 may have radii that are generally equivalent to the radii of the medial-lateral curvatures 220 of the talar bone engagement surface 112 of the talar prosthesis 102.

The shape of the cutting element 720 of the burr 610 may determine the parameters of the various constituent shapes of the prepared surface 620. Specifically, the radius 782 along the length of the cutting tool axis 740 of the cutting element 720 of the burr 610 may be substantially the same as the radius of the convex anterior-posterior curvature 1100. Similarly, the maximum radius 780 perpendicular to cutting tool axis 740 of the cutting element 720 of the burr 610 may be substantially the same as the radii of the concave medial-lateral curvatures 1130.

As mentioned previously, it may be desirable to form a slot in the prepared surface 620 so that the surface 620 may securely receive the keel 212 of the talar prosthesis 102.

Formation of a slot is optional; in some embodiments, an ankle prosthesis may not have a keel, or may have a keel with built-in cutting elements that form a slot in response to pressure of the keel against the bone. Further, in some embodiments, the slot may be formed prior to formation of the remainder of the prepared surface 620. Thus, for example, the burr 800 may be used to form the slot prior to use of the burr 610 to form the prepared surface 620 depicted in FIGS. 11A and 11B, and may even be used to form the slot prior to use of the burr 830. Formation of the slot will be depicted in FIG. 12, under the assumption that the prepared surface 620 has already been formed as shown in FIGS. 11A and 11B.

Figure 12:
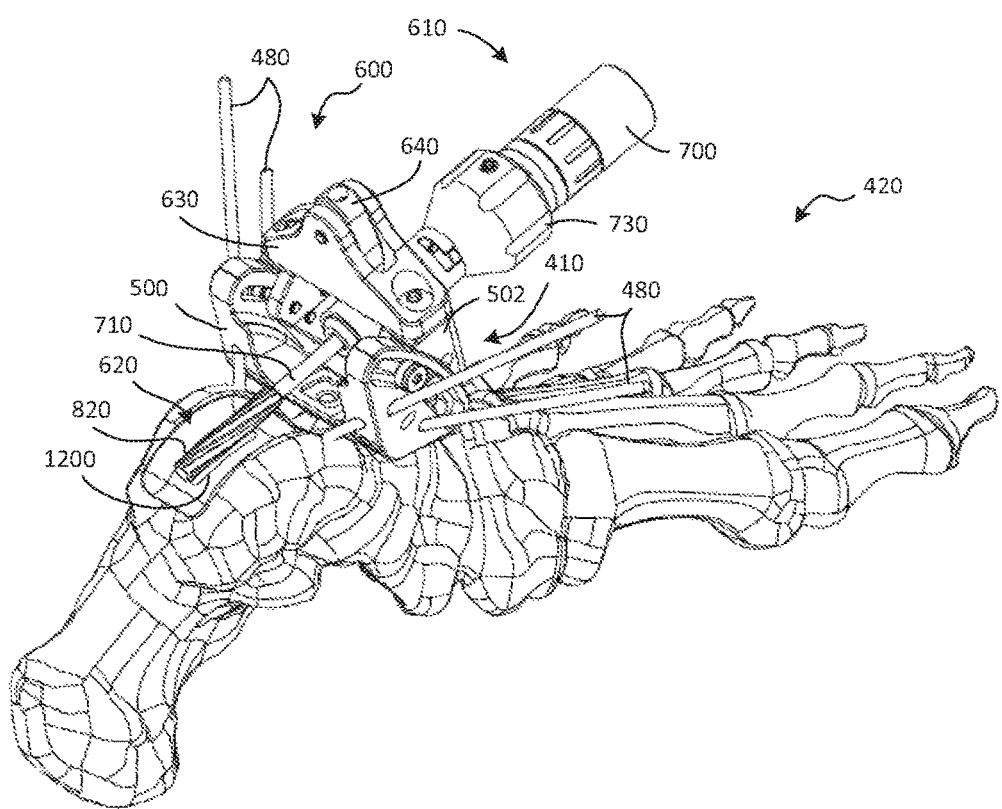
FIG. 12 is a perspective view depicting formation of a slot in the prepared surface of the talus, using the burr.

FIG. 12 is a perspective view depicting formation of a slot 1200 in the prepared surface 620 of the talus 420, using the burr 800. After the completion of previous bone removal steps (or optionally, prior to the performance of such steps, as described above), the burr 800 may be attached to the attachment cannula 970 of the talar burr holder 600, with the talar burr holder 600 secured to the mobile member 502 of the talar foundation 410. The burr 800 may then be positioned over the central portion of the prepared surface 620. The surgeon may hold the burr 800 above the prepared surface 620 against the force of the linear spring 954. Again, the post 980 may be displaced from the guide surface 932 at the bottom of the rectangular window 930 until the surgeon is ready to begin forming the slot in the prepared surface 620 with the burr 800.

The surgeon may then hold the burr 800 in a central position medial-laterally, and lower the burr 800, allowing the linear spring 954 to press the burr 800 to engage the prepared surface 620, until the post 980 rests against the guide surface 932 at the bottom of the rectangular window 930. This is the position depicted in FIG. 12. As the cutting element 820 of the burr 800 is lowered into the prepared surface 620, the cutting element 820 may form a slot 1200 substantially in the center of the prepared surface 620. The diameter 822 of the cutting element 820 may be generally equivalent to the width of the keel 212 of the talar prosthesis 102. The slot 1200 may have a caudal end (not visible) with a generally hemispherical, concave cross-sectional shape that snugly receives the semicircular perimeter 244 of the penetrating portion 242 of the keel 212.

The keel 212 may interface with the slot 1200 in a manner that helps prevent the talar prosthesis 102 from moving medial-laterally relative to the prepared surface 620, and further facilitates secure adherence of the talar prosthesis 102 to the prepared surface 620. The keel 212 and/or the remainder of the talar bone engagement surface 112 of the talar prosthesis 102 may optionally have a porous surface and/or a coated surface designed to promote bone in-growth and adhesion. Additionally or alternatively, the talar prosthesis 102 may be designed for use with a bone cement that forms a bond between the talus 420 and the talar prosthesis 102.

Once the prepared surface 620 has been fully formed, including the slot 1200, the talar burr holder 600 may be removed from the talar foundation 410, along with any attached cutting tool. The talar foundation 410 may remain in place on the talus 420, as in FIG. 5C. Then, the talar foundation 410 may be used to facilitate attachment of a tibial cutting guide to a tibia, as depicted in FIGS. 13A through 13C.

FIGS. 13A through 13C are posterior caudal perspective, anterior elevation, and anterior cephalad perspective views, respectively, of a tibial foundation 1300, with an alignment block 1310 also depicted in FIG. 13C to secure the tibial foundation 1300 to a tibia 1320. The talar foundation 410 may remain secured to the talus 420, as shown, and the alignment block 1310 may be attached to the talar foundation 410 and to the tibial foundation 1300 so that the tibial foundation 1300 is positioned properly relative to the joint.

Like the talar foundation 410, the tibial foundation 1300 may be part of a cutting guide that helps to guide a cutting tool relative to bone. A cutting tool holder such as a tibial burr holder may be attached to the tibial foundation 1300, as will be shown and described subsequently.

The tibial foundation 1300 may have a bone attachment interface that facilitates attachment of the tibial foundation 1300 to the tibia 1320. Any bone attachment feature known in the art may be used; in the embodiment of FIGS. 13A through 13C, the bone attachment interface may take the form of a series of passageways 1330 through which the pins 480 are inserted. As in the talar foundation 410, the passageways 1330 may be oriented obliquely relative to each other so that the pins 480 are nonparallel to each other. Thus, when the pins 480 are in place, the position and orientation of the tibial foundation 1300 may substantially fixed relative to the tibia 1320. There may be more of the passageways 1330 than are needed for fixation of the tibial foundation 1300; accordingly, the surgeon may only insert the pins 480 through the passageways 1330 that are positioned for optimal anchorage of the pins 480 in the tibia 1320.

The tibial foundation 1300 may also have a tool holder attachment interface, or more specifically, a tibial burr holder interface attachable to a tibial burr holder that holds a cutting tool in the form of a burr. The tibial burr holder may have a base that is attachable to the talar burr holder interface; thus, the tibial burr holder interface may also be called a base attachment interface. The base attachment interface may be designed to secure the base relative to the tibial foundation 1300. Unlike the talar foundation 410, the tibial foundation 1300 may not have a stationary member and a mobile member; rather, the entirety of the tibial foundation may act as a stationary base for registration of the tibial burr holder. As depicted in FIG. 13C, the base attachment interface may also be used to attach the tibial foundation 1300 to the alignment block 1310 to facilitate positioning of the tibial foundation 1300 relative to the tibia 1320.

In FIGS. 13A through 13C, the base attachment interface may take the form of a button 1340 with a threaded hole 1342, which may receive the threaded tip of a fastener to attach the tibial burr holder or the alignment block to the button 1340. The button 1340 may also have an anterior rim 1344 and a posterior rim 1346 that cooperate to engage a slot 1350. More precisely, the slot 1350 may have a ledge 1352 that defines a keyhole shape of the slot 1350. The ledge 1352 may reside between the anterior rim 1344 and the posterior rim 1346 such that the button 1340 can slide upward or downward within the slot 1350. The slot 1350 may have a cephalad end 1354 in which the ledge 1352 is not present. The cephalad end 1354 may thus provide a circular opening through which the anterior rim 1344 and the posterior rim 1346 can be inserted to permit assembly of the button into a plate 1360 in which the slot 1350 is formed.

As shown in FIG. 13C, the alignment block 1310 may have a body 1370 with a talar foundation interface attachable to the talar foundation 410, and a tibial foundation interface attachable to the tibial foundation 1300. Each foundation interface may provide secure fixation with the corresponding foundation so that the talar foundation 410 and the tibial foundation 1300 can be secured together at predictable relative positions.

As embodied in FIG. 13C, the talar foundation interface may include two holes 1380 configured similarly to the two holes 900 of the talar burr holder 600. The holes 1380 may be spaced apart in a manner similar to that of the threaded holes 550 of the mobile member 502 of the talar foundation 410, and may be smooth-bored. Accordingly, fasteners like the fasteners 902 of the talar burr holder 600, which may be screws, bolts, or the like, may be inserted through the holes 1380 and rotated into engagement with the threaded holes 550 of the mobile member 502 of the talar foundation 410 to secure the alignment block 1310 to the mobile member 502.

The tibial foundation interface may include a hole 1390, which may be smooth-bored like the holes 1380. A fastener like the fasteners 902 of the talar burr holder 600, which may be a screw, bolt, or the like, may be inserted through the hole 1390 and rotated into engagement with the hole 1342 of the tibial foundation 1300 to secure the tibial foundation 1300 to the alignment block 1310.

The alignment block 1310 may first be secured to the talar foundation 410 by securing the holes 1380 to the threaded holes 550 of the mobile member 502, for example, with the fasteners 902. The mobile member 502 may be positioned at a predictable location, such as at the anterior end of its range of motion relative to the stationary member 500, as the alignment block 1310 is attached to it. If desired, the mobile member 502 may be locked in place relative to the stationary member 500, for example, through the use of the guide knob 540.

The tibial foundation 1300 may then be secured to the alignment block 1310 by securing the hole 1390 to the hole 1342 of the tibial foundation 1300, for example, with a fastener such as a screw or bolt. In alternative embodiments, the alignment block 1310 may be secured to the tibial foundation 1300 first, and then to the talar foundation 410.

In either case, after attachment of the alignment block 1310 to the talar foundation 410 and the tibial foundation 1300, the tibial foundation 1300 may be at a predictable location relative to the talar foundation 410, and thence, relative to the ankle joint. Thus, the tibial foundation 1300 may be used to guide resection of the tibia 1320. The tibial foundation 1300 may thus be secured to the tibia 1320 as shown, by inserting pins 480 through the passageways 1330 of the tibial foundation 1300, and anchoring the distal ends of the pins 480 in the bone of the tibia 1320. Once the tibial foundation 1300 has been anchored to the tibia 1320, the alignment block 1310 may be detached from the talar foundation 410 and the tibial foundation 1300. The talar foundation 410 may also be detached from the talus 420 by withdrawing the pins 480 from the talus 420.

The tibial foundation 1300 may then be used in combination with a tibial burr holder to define a tibial guide assembly that guides the burr relative to the tibia. This will be described in greater detail in connection with FIGS. 14A through 14C.

Figure 15:
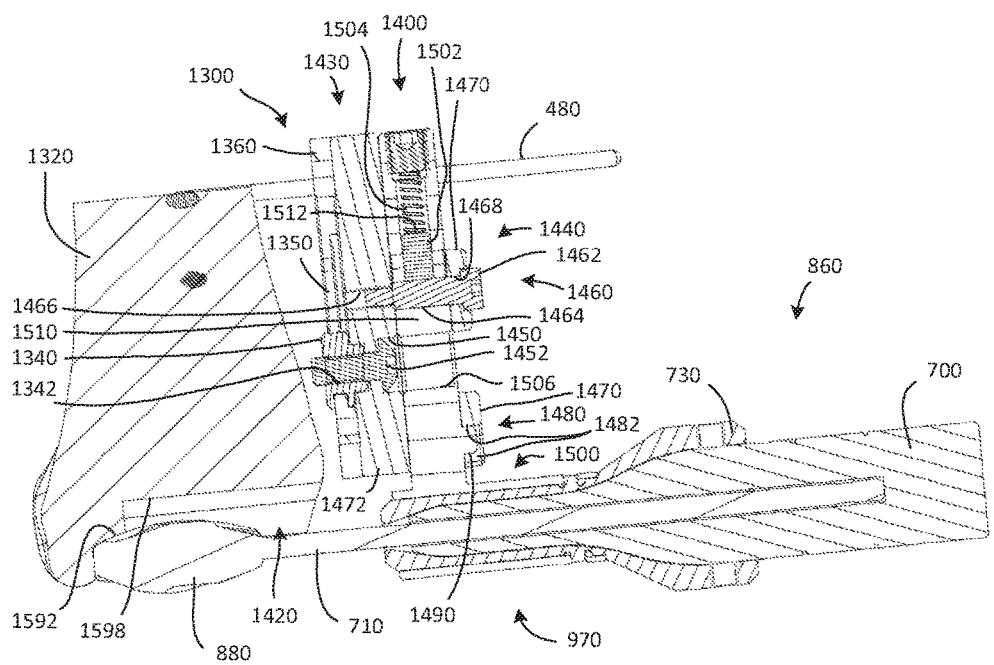
FIG. 15 is a lateral elevation, section view of the tibial burr holder and the tibial foundation, secured to the tibia.

FIGS. 14A, 14B, and 14C are anterior cephalad perspective, lateral elevation, and anterior cephalad perspective views, respectively, of a tibial burr holder 1400, with the tibial burr holder 1400 secured to the tibial foundation 1300 and the tibia 1320 in FIG. 14C. The tibial foundation 1300 and the tibial burr holder 1400, combined, may define a tibial guide assembly that guides motion of the burr 860 relative to the tibia 1320 to form a prepared surface on the tibia 1320 that is shaped to receive a prosthesis, such as the tibial prosthesis 104 of FIGS. 1A through 1C and 3A through 3E. Further, FIG. 15 is a lateral elevation, section view of the tibial burr holder 1400 and the tibial foundation 1300, secured to the tibia 1320. The configuration and operation of the tibial burr holder will be set forth in connection with FIGS. 14A through 15.

Specifically, the tibial burr holder 1400 may be secured to the hole 1390 of the tibial foundation 1300. The tibial burr holder 1400 may enable motion (for example, medial-laterally and cephalad-caudally) of the burr 860 to generate the desired contour of a prepared surface 1420 (shown in FIG. 15) of the tibia 1320. Use of the burr 860 is merely exemplary; those of skill in the art will recognize that a wide variety of cutting tools may be used to form the prepared surface 1420. Such cutting tools may include rotating and/or translating tools such as burrs, reamers, reciprocating saws, and/or the like.

As shown, the tibial burr holder 1400 may have a base 1430 that is fixedly secured to the tibial foundation 1300, and an arm 1440 that moves relative to the base 1430. Motion of the arm 1440 relative to the base 1430 may enable the burr 860 to move medial-laterally on the tibia 1320. The base 1430 and the arm 1440 may cooperate to provide constrained motion of a cutting tool relative to the tibia 1320, in a manner similar to that of the talar burr holder 600, as will be described below.

The base 1430 of the tibial burr holder 1400 may have a foundation interface that can be used to attach the base 1430 to the tibial foundation 1300. The foundation interface may have any structure suitable for securing the base 1430 to the tibial foundation 1300. As embodied in FIGS. 14A through 15, the foundation interface may include a hole 1450 that can be aligned with the hole 1342 of the button 1340 of the tibial foundation 1300 such that a fastener 1452, such as a screw or bolt, can be inserted through the hole 1450 and rotated into engagement with the hole 1342 of the button 1340 of the tibial foundation 1300 to secure the base 1430 to the tibial foundation 1300.

The base 1430 may further have an arm coupling feature by which the arm 1440 is coupled to the base 1430. The base 1430 and the arm 1440 may be movably coupled together through any combination of rotating and/or sliding joints. According to some embodiments, the arm coupling feature provides a rotatable coupling between the base 1430 and the arm 1440.

As shown in FIGS. 14A through 15, the arm coupling feature may include a pin 1460 about which the arm 1440 is rotatably mounted. The pin 1460 may have a head 1462 and a shank 1464 with male threads that can engage corresponding female threads in a hole 1466 in the base 1430. The head 1462 may have an interface that permits rotation of the head 1462 with a tool such as a screwdriver to facilitate assembly of the tibial burr holder 1400. The head 1462 may reside within a hole 1468 in the base 1430. A portion of the shank 1464 adjacent to the head 1462 may be smooth so that the arm 1440 can engage and rotate smoothly on it. The base 1430 may further have two anterior plates 1470 and a posterior plate 1472, between which the arm 1440 is generally captured. The hole 1468 in which the head 1462 resides may be formed in the topmost of the anterior plates 1470, and the hole 1466 in which the shank 1464 is anchored may be formed in the posterior plate 1472. Thus, the pin 1460 may be inserted posteriorly, through the hole 1468 in the topmost of the anterior plates 1470 to anchor in the hole 1466 in the posterior plate 1472.

Further, the base 1430 may have a base guide feature that helps to guide motion of the arm 1440 relative to the base 1430. The base guide feature may cooperate with a corresponding arm guide feature of the arm 1440 to limit the range of motion of the arm 1440, thereby limiting the range of motion of the attached cutting tool, such as the burr 860, the burr 800, or the burr 830, relative to the tibia 1320. As embodied in FIGS. 14A through 15, the base guide feature may include a notch 1480 with a plurality of guide surfaces 1482. One of the guide surfaces 1482 may be oriented to face in the caudal direction to limit motion of the cutting tool in the cephalad direction toward the tibia 1320, as will be described subsequently. The remaining guide surfaces 1482 may be oriented medial-laterally to limit motion of the cutting tool in the medial and lateral directions.

As shown in FIG. 15, the arm 1440 may be divided into a first arm member 1500 and a second arm member 1502. The second arm member 1502 may be nested within the first arm member 1500 such that the second arm member 1502 is slidable within the first arm member 1500 so that the arm 1440 effectively has adjustable reach relative to the pin 1460. A resilient member may be used to bias the first arm member 1500 apart from the second arm member 1502, thereby urging the arm 1440 toward its maximum length. The resilient member may take the form of a linear spring 1504 that is normally held under compression. The linear spring 1504 may reside partially in a cavity in the distal end of the second arm member 1502. The first arm member 1500 may have an aperture 1506 through which the fastener 1452 is accessible from anterior to the tibial burr holder 1400.

The arm 1440 may have a base coupling feature by which the arm 1440 is coupled to the base 1430. The base coupling feature may be configured in a variety of ways, and may be designed to cooperate with the arm coupling feature of the base 1430. In FIG. 15, the base coupling feature may include a slot 1510 formed in the first arm member 1500, and a cradle 1512 formed in the top end of the second arm member 1502. The slot 1510 may be elongated cephalad-caudally, and may receive the pin 1460 to allow the first arm member 1500 to move upward or downward relative to the pin 1460. The cradle 1512 may be concave and semicircular in shape so that the top end of the second arm member 1502 abuts and slides relatively smoothly relative to the pin 1460, while permitting the end of the second arm member 1502 to push downward against the pin 1460, urging the first arm member 1500 upward.

The arm 1440 may further have a tool attachment interface to which a cutting tool can be attached. Where the cutting tool is a burr such as the burr 610, the burr 800, the burr 830, and/or the burr 860, the tool attachment interface may be referred to as a burr attachment interface. The burr attachment interface may be designed to hold any of the burr 860, the burr 800, and the burr 830 in a fixed relationship to the first arm member 1500. More precisely, the burr attachment interface may be designed to receive and secure the adapter 730 secured to one of the burr 860, the burr 800, and the burr 830.

As depicted in FIGS. 14A through 15, the burr attachment interface may take the form of an attachment cannula 970 that is substantially identical to the attachment cannula 970 of the talar burr holder 600. Thus, the attachment cannula 970 of the tibial burr holder 1400 may have a bore 972 sized to receive the cylindrical distal end 792 of the adapter 730. The attachment cannula 970 may also have one or more locking features that can selectively lock the adapter 730 in place relative to the attachment cannula 970. The locking features may operate as bayonet fittings; thus, they may take the form of slots 974 that extend axially, and then circumferentially, on the attachment cannula. Each of the slots 974 may be sized to receive one of the burr holder attachment bosses 796 of the adapter 730. The adapter maybe received in and interlocked with the attachment cannula 970 as described in connection with the talar burr holder 600.

Yet further, the arm 1440 may have an arm guide feature that cooperates with the base guide feature to constrain motion of the arm 1440 relative to the base 1430. The arm guide feature may be any member that can interact with the base guide feature to help constrain relative motion between the base 1430 and the arm 1440. Where the base guide feature includes guide surfaces, the arm guide feature may advantageously be a follower that can abut and/or rest against such guide surfaces.

Specifically, the base guide feature may be a post 1490 protruding from the first arm member 1500, between the pin 1460 and the attachment cannula 970. The post 1490 may protrude anteriorly such that the post 1490 resides in the notch 1480. The interaction of the post 1490 with the guide surface 1482 of the notch 1480 may limit motion of the attachment cannula 970, and thence the cutting tool, to a generally rectangular zone. In particular, the guide surface 1482 on the top of the notch 1480 may limit motion of the cutting tool toward the tibia 1320, thereby controlling the depth of the resection.

More particularly, the guide surface 1482 on the top of the notch 1480 may prevent the cutting tool axis 740 of the burr 860, the burr 800, or the burr 830 from moving closer to the tibia 1320 than a planar boundary. Similarly, the guide surfaces 1482 on the sides of the notch 1480 may prevent the cutting tool axis 740 of the burr 860, the burr 800, or the burr 830 from moving further medially or laterally than additional planar boundaries. Thus, the post 1490 of the arm 1440 may cooperate with the notch 1480 of the base 1430 to ensure that the prepared surface 1420 has the desired depth, width, and overall shape.

The action of the linear spring 1504 may also help ensure that the prepared surface 1420 has the desired shape. Specifically, the pressure exerted by the linear spring 1504 may help ensure that cuts made to the tibia 1320 extend to the full desired depth, thereby ensuring that the prepared surface 1420 has the depth and consistency needed to provide a continuous expanse of bone to support the tibial prosthesis 104. Nevertheless, the linear spring 1504 may be tuned to provide force that can easily be resisted by the surgeon in order to remove bone with shallower cuts prior to extending the cutting tool to the full depth permitted by the interaction of the post 1490 with the notch 1480.

The tibial burr holder 1400 may be employed in a manner similar to that of the talar burr holder 600 to form the prepared surface 1420 on the distal end of the tibia 1320, except that the tibial burr holder 1400 has no movable member, so there is no need to move the cutting tool anterior-posteriorly. Rather, the cuts may all be made at the same anterior-posterior reference. Cutting may optionally begin with the burr 830 to remove sufficient bone to make room for the shaft 710 of the burr 860, and then cutting may continue with the burr 860 to form the contours of the prepared surface 1420, aside from the slot for the keel 312 of the tibial prosthesis 104. The burr 800 may be used to form such a slot.

As with the talar burr holder 600, the linear spring 1504 may be used to help ensure that the proper depth of cut is obtained. Specifically, the surgeon may position the cutting element 850 of the burr 830 under the natural articular surface of the tibia 1320. The surgeon may hold the burr 830 below the natural articular surface, against the force of the linear spring 1504, with the post 1490 displaced below the guide surface 1482 at the top of the notch 1480, until he or she is ready to begin resecting the natural articular surface.

The surgeon may then allow the burr 830 to rise, allowing the linear spring 1504 to press the burr 830 to engage the natural articular surface, until the post 1490 rests against the guide surface 1482 at the top of the notch 1480. The burr 830 may then be moved medial-laterally (i.e., from side-to-side) by moving the attachment cannula 970 medial-laterally, causing the post 1490 to slide medial-laterally along the guide surface 1482 at the top of the notch 1480. The post 1490 may abut the guide surfaces 1482 at the left and right sides of the notch 1480 to control the extent of medial-lateral motion of the burr 830.

Once the burr 830 has passed over the medial-lateral extents of the natural articular surface, the burr 830 may be removed from the attachment cannula 970, and the burr 860 may instead be secured to the attachment cannula 970. The burr 860 may then be positioned under the natural articular surface of the tibia 1320. The surgeon may hold the burr 860 below the natural articular surface, which has now been partially resected, against the force of the linear spring 1504. Again, the post 1490 may be displaced from the guide surface 1482 at the top of the notch 1480 until the surgeon is ready to begin resecting the natural articular surface with the burr 860.

The surgeon may then raise the burr 860, allowing the linear spring 1504 to press the burr 860 to engage the natural articular surface, until the post 1490 rests against the guide surface 1482 at the top of the notch 1480. The burr 860 may then be moved medial-laterally (i.e., from side-to-side) by moving the attachment cannula 970 medial-laterally, causing the post 1490 to once again slide medial-laterally along the guide surface 1482 at the top of the notch 1480. The post 1490 may abut the guide surfaces 1482 at the left and right sides of the notch 1480 to control the extent of medial-lateral motion of the burr 860.

The prepared surface 1420 may then have a shape similar to that of the prepared surface 620 of the talus 420, but with a concave anterior-posterior curvature 1592 in place of the convex anterior-posterior curvature 1100. A portion of the concave anterior-posterior curvature 1592 is depicted in FIG. 15. Referring briefly back to FIG. 11B, the prepared surface 1420 may have, in a plane parallel to the anterior-posterior direction 130 and the cephalad-caudal direction 134, in addition to the concave anterior-posterior curvature 1592, two convex anterior-posterior curvatures 1110 located anterior to and posterior to the concave anterior-posterior curvature 1592. Further, in a plane parallel to the medial-lateral direction 132 and the cephalad-caudal direction 134, the prepared surface 1420 may have a central expanse 1120 and two concave medial-lateral curvatures 1130 positioned on either side of the central expanse 1120. Thus, once a slot is formed for the keel 312, the prepared surface 1420 may have a shape that generally complements the shape of the tibial bone engagement surface 122 of the tibial prosthesis 104, as depicted in FIGS. 3A through 3E.

Once the burr 860 has been passed over the medial-lateral extents of the natural articular surface, the burr 860 may be removed from the attachment cannula 970, and the burr 800 may instead be secured thereto. The burr 800 may then be positioned under the central portion of the prepared surface 1420. The surgeon may hold the burr 800 beneath the prepared surface 1420 against the force of the linear spring 1504. Again, the post 1490 may be displaced from the guide surface 1482 at the top of the notch 1480 until the surgeon is ready to begin forming the slot in the prepared surface 1420 with the burr 800.

The surgeon may then hold the burr 800 in a central position medial-laterally, and raise the burr 800, allowing the linear spring 1504 to press the burr 800 to engage the prepared surface 1420, until the post 1490 rests against the guide surface 1482 at the top of the notch 1480. As the cutting element 820 of the burr 800 is raised into the prepared surface 1420, the cutting element 820 may form a slot 1598 substantially in the center of the prepared surface 1420. The diameter 822 of the cutting element 820 may be generally equivalent to the width of the keel 312 of the tibial prosthesis 104. The slot 1598 may have a cephalad end with a generally hemispherical, concave cross-sectional shape that snugly receives the semicircular perimeter 344 of the penetrating portion 342 of the keel 312.

The keel 312 may interface with the slot 1598 in a manner that helps prevent the tibial prosthesis 104 from moving medial-laterally relative to the prepared surface 1420, and further facilitates secure adherence of the tibial prosthesis 104 to the prepared surface 1420. The keel 312 and/or the remainder of the tibial bone engagement surface 122 of the tibial prosthesis 104 may optionally have a porous surface and/or a coated surface designed to promote bone in-growth and adhesion. Additionally or alternatively, the tibial prosthesis 104 may be designed for use with a bone cement that forms a bond between the tibia 1320 and the tibial prosthesis 104.

Once the prepared surface 1420 has been fully formed, including the slot 1598, the tibial foundation 1300 may be removed from the tibial foundation 1300, along with any attached cutting tool. The tibial foundation 1300 may also be removed from the tibia 1320 in order to clear any obstruction from the joint space. Then, the talar prosthesis 102 and the tibial prosthesis 104 may be positioned on the prepared surface 620 of the talus 420 and on the prepared surface 1420 of the tibia 1320, respectively. The resulting configuration will be shown and described in connection with FIG. 16.

Figure 16:
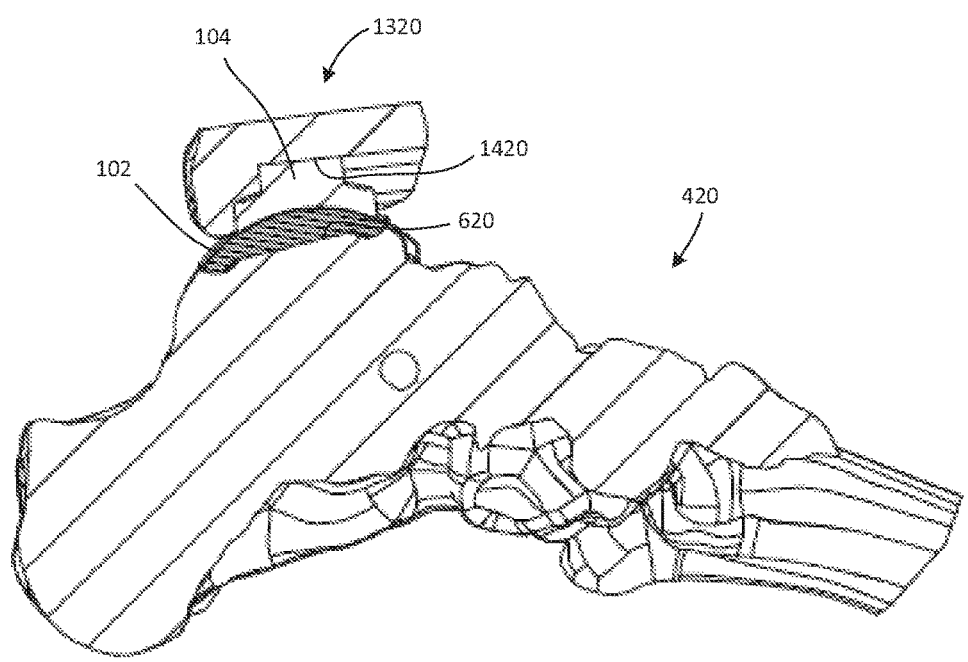
FIG. 16 is a lateral elevation, section view depicting the talus and the tibia, with the talar prosthesis secured to the prepared surface of the talus, and the tibial prosthesis secured to the prepared surface of the tibia.

FIG. 16 is a lateral elevation, section view depicting the talus 420 and the tibia 1320, with the talar prosthesis 102 secured to the prepared surface 620 of the talus 420, and the tibial prosthesis 104 secured to the prepared surface 1420 of the tibia 1320. The talar articular surface 110 may articulate with the tibial articular surface 120 in a manner that generally mimics the articulation of the natural ankle joint. The various curvatures of the prepared surface 620 and the prepared surface 1420, along with the matching curvatures of the talar bone engagement surface 112 and the tibial bone engagement surface 122, may help keep the talar prosthesis 102 and the tibial prosthesis 104 in place, while preserving sufficient healthy bone to tolerate the stresses incurred during use of the joint.

In some embodiments (not shown), surgical navigation and/or surgical robotics systems may be used to facilitate preparation of the talus 420 and/or the tibia 1320. Some of the steps set forth above may be automated. Surgical navigation systems, surface mapping systems, and/or the like may be used to ascertain the locations and dimensions of the cuts to be made. The motion pathways for the cuts to the talus 420 and the tibia 1320 may optionally be mechanized, for example, using motorized systems in addition to or in place of elements of the talar guide assembly and/or the tibial guide assembly. Such motorized systems may optionally mimic the motion constraints of the talar guide assembly and/or the tibial guide assembly, and may thus access and prepare the joint surfaces from an anterior approach as disclosed herein.

Those of skill in the art will recognize that the systems and methods set forth previously represent only some of the systems and methods by which ankle arthroplasty may be carried out. Alternative methods, cutting tools, guide assemblies, and implants may be used within the scope of the present disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. Claim elements that do not include the word "means" are not intended to be construed under 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. An ankle arthroplasty system comprising:
a talar joint prosthesis comprising:
a talar articular surface shaped to replace a natural talar articular surface; and
a talar bone engagement surface shaped to engage a talar prepared surface of a talus;
a tibial joint prosthesis comprising:
a tibial articular surface shaped to replace a natural tibial articular surface and to articulate with the talar articular surface; and
a tibial bone engagement surface shaped to engage a tibial prepared surface of a tibia;
wherein at least one selection from the group consisting of the tibial bone engagement surface and the talar bone engagement surface comprises:
a first anterior-posterior curvature extending in an anterior-posterior direction; and
a first medial-lateral curvature positioned at a medial edge or a lateral edge of the tibial bone engagement surface or the talar bone engagement surface, the first medial-lateral curvature having a convex shape and extending in a medial-lateral direction;
wherein:
the talar articular surface or tibial articular surface associated with the selection comprises an articular medial-lateral curvature positioned at a medial edge or a lateral edge of the talar articular surface or the tibial articular surface and extending in the medial-lateral direction; and
the first medial-lateral curvature has a greater radius of curvature than the articular medial-lateral curvature.

2. The ankle arthroplasty system of claim 1, wherein the selection further comprises a keel protruding from the first anterior-posterior curvature and extending along the anterior-posterior direction, wherein the keel comprises:
a base portion secured or integrally formed with a remainder of the selection; and
a penetrating portion extending from the base portion to penetrate the talar prepared surface or the tibial prepared surface, the penetrating portion having a generally semicircular perimeter.

3. The ankle arthroplasty system of claim 1, wherein:
the talar articular surface comprises:
two convex talar curvatures extending in the medial-lateral direction; and
a concave talar curvature extending in the medial-lateral direction, between the two convex talar curvatures;
the tibial articular surface comprises:
two concave tibial curvatures extending in the medial-lateral direction; and
a convex tibial curvature extending in the medial-lateral direction, between the two concave tibial curvatures; and
the talar articular surface and the tibial articular surface are further shaped such that, with the tibial joint prosthesis centered on the talar joint prosthesis, the two concave tibial curvatures lie substantially flush with the two convex talar curvatures.

4. The ankle arthroplasty system of claim 1, wherein:
the first medial-lateral curvature extends along the anterior-posterior direction across a majority of the selection.

5. The ankle arthroplasty system of claim 4, wherein the selection further comprises:
a second medial-lateral curvature having a convex shape and extending in the medial-lateral direction; and
a central expanse extending in a substantially straight line, generally parallel to the medial-lateral direction, between the first medial-lateral curvature and the second medial-lateral curvature.

6. The ankle arthroplasty system of claim 5, wherein the selection further comprises a keel protruding from the first anterior-posterior curvature and extending along the anterior-posterior direction.

7. The ankle arthroplasty system of claim 1, wherein:
the selection comprises the tibial bone engagement surface; and
the first anterior-posterior curvature comprises a convex shape.

8. The ankle arthroplasty system of claim 7, wherein the tibial bone engagement surface further comprises:

a second medial-lateral curvature having a convex shape and extending in the medial-lateral direction; and a central expanse extending in a substantially straight line, generally parallel to the medial-lateral direction, between the first medial-lateral curvature and the second medial-lateral curvature.

9. The ankle arthroplasty system of claim 8, wherein the tibial bone engagement surface further comprises a keel protruding from the first anterior-posterior curvature and extending along the anterior-posterior direction.

10. An ankle arthroplasty system comprising:
a talar joint prosthesis comprising:
a talar articular surface shaped to replace a natural talar articular surface; and
a talar bone engagement surface shaped to engage a talar prepared surface of a talus;
a tibial joint prosthesis comprising:
a tibial articular surface shaped to replace a natural tibial articular surface and to articulate with the talar articular surface; and
a tibial bone engagement surface shaped to engage a tibial prepared surface of a tibia;
wherein the talar bone engagement surface comprises:
a first anterior-posterior curvature having a concave shape and extending in an anterior-posterior direction;
a first medial-lateral curvature having a convex shape and extending in a medial lateral direction;
a second medial-lateral curvature having a convex shape and extending in the medial-lateral direction; and
a central expanse extending in a substantially straight line, generally parallel to the medial-lateral direction, between the first medial-lateral curvature and the second medial-lateral curvature;
wherein the talar bone engagement surface further comprises a keel protruding from the first anterior-posterior curvature, the keel having a length extending from an anterior portion of the first anterior-posterior curvature across a central portion to a posterior portion of the first anterior-posterior curvature;
wherein the first anterior-posterior curvature extends along substantially an entire length, in the anterior-posterior direction, of the talar bone engagement surface.

11. The ankle arthroplasty system of claim 10, wherein the keel is configured to slide anterior-posteriorly along the talar prepared surface.

12. The ankle arthroplasty system of claim 11, wherein the keel further comprises:
a base portion secured or integrally formed with a remainder of the talar bone engagement surface; and
a penetrating portion extending from the base portion, the penetrating portion having a generally semicircular perimeter.

13. A method for ankle arthroplasty comprising:
positioning a talar joint prosthesis proximate a talus, the talar joint prosthesis comprising:
a talar articular surface shaped to replace a natural talar articular surface; and
a talar bone engagement surface shaped to engage a talar prepared surface of a talus;
positioning a tibial joint prosthesis proximate a tibia, the tibial joint prosthesis comprising:
a tibial articular surface shaped to replace a natural tibial articular surface and to articulate with the talar articular surface; and
a tibial bone engagement surface shaped to engage a tibial prepared surface of a tibia;
wherein at least one selection from the group consisting of the talar bone engagement surface and the tibial bone engagement surface comprises:
a first anterior-posterior curvature extending in an anterior-posterior direction; and
a first medial-lateral curvature having a convex shape and extending in a medial-lateral direction;
performing at least one action selected from the group consisting of:
inserting the talar joint prosthesis into a joint space between the talus and the tibia along the anterior-posterior direction such that the talar bone engagement surface slides along the talar prepared surface; and
inserting the tibial joint prosthesis into the joint space along the anterior-posterior direction such that the tibial bone engagement surface slides along the tibial prepared surface;
wherein the first anterior-posterior curvature extends along substantially an entire length, in the anterior-posterior direction, of the selection.

14. The method of claim 13, wherein selection further comprises:
a second medial-lateral curvature having a convex shape and extending in the medial-lateral direction; and
a central expanse extending in a substantially straight line, generally parallel to the medial-lateral direction, between the first medial-lateral curvature and the second medial-lateral curvature.

15. The method of claim 14, wherein selection further comprises a keel protruding from the first anterior-posterior curvature and extending along the anterior-posterior direction.

16. The method of claim 15, wherein the keel comprises:
a base portion secured or integrally formed with a remainder of the selection; and
a penetrating portion extending from the base portion, the penetrating portion having a generally semicircular perimeter.

17. An ankle arthroplasty system comprising:
a talar joint prosthesis comprising:
a talar articular surface shaped to replace a natural talar articular surface; and
a talar bone engagement surface shaped to engage a talar prepared surface of a talus;
a tibial joint prosthesis comprising:
a tibial articular surface shaped to replace a natural tibial articular surface and to articulate with the talar articular surface; and
a tibial bone engagement surface shaped to engage a tibial prepared surface of a tibia;
wherein the tibial bone engagement surface comprises:
a first anterior-posterior curvature extending in an anterior-posterior direction; and
a first medial-lateral curvature having a convex shape and extending in a medial-lateral direction;
wherein the first medial-lateral curvature extends along the anterior-posterior direction across a majority of the tibial bone engagement surface.

18. The ankle arthroplasty system of claim 17, wherein the first anterior-posterior curvature extends along substantially an entire length, in the anterior-posterior direction, of the tibial bone engagement surface.

19. The ankle arthroplasty system of claim 17, wherein the tibial bone engagement surface further comprises a keel protruding from the first anterior-posterior curvature and extending along the anterior-posterior direction, wherein the keel comprises:
    a base portion secured or integrally formed with a remainder of the tibial bone engagement surface; and
    a penetrating portion extending from the base portion to penetrate the tibial prepared surface, the penetrating portion having a generally semicircular perimeter.

20. The ankle arthroplasty system of claim 17, wherein:
the talar articular surface comprises:
    two convex talar curvatures extending in the medial-lateral direction; and
    a concave talar curvature extending in the medial-lateral direction, between the two convex talar curvatures;
the tibial articular surface comprises:
    two concave tibial curvatures extending in the medial-lateral direction; and
    a convex tibial curvature extending in the medial-lateral direction, between the two concave tibial curvatures; and
the talar articular surface and the tibial articular surface are further shaped such that, with the tibial joint prosthesis centered on the talar joint prosthesis, the two concave tibial curvatures lie substantially flush with the two convex talar curvatures.

21. The ankle arthroplasty system of claim 17, wherein the tibial bone engagement surface further comprises:
    a second medial-lateral curvature having a convex shape and extending in the medial-lateral direction; and
    a central expanse extending in a substantially straight line, generally parallel to the medial-lateral direction, between the first medial-lateral curvature and the second medial-lateral curvature.

22. The ankle arthroplasty system of claim 21, wherein the tibial bone engagement surface further comprises a keel protruding from the first anterior-posterior curvature and extending along the anterior-posterior direction.

23. The ankle arthroplasty system of claim 17, wherein the first anterior-posterior curvature comprises a convex shape.

24. The ankle arthroplasty system of claim 23, wherein the talar bone engagement surface comprises:
    A first anterior-posterior curvature extending in the anterior-posterior direction, the first anterior-posterior curvature comprising a concave curvature;
    a first medial-lateral curvature and a second medial-lateral curvature, each of which has a convex shape and extends in the medial-lateral direction; and
    a central expanse extending in a substantially straight line, generally parallel to the medial-lateral direction, between the first medial-lateral curvature and the second medial-lateral curvature.

25. The ankle arthroplasty system of claim 24, wherein the talar bone engagement surface further comprises a keel protruding from the first anterior-posterior curvature and extending along the anterior-posterior direction.

\* \* \* \* \*